(12) United States Patent
Watanabe et al.

(10) Patent No.: US 12,311,082 B2
(45) Date of Patent: May 27, 2025

(54) INFORMATION PROCESSING SYSTEM, NON-TRANSITORY COMPUTER READABLE MEDIUM, AND BOOTH

(71) Applicant: FUJIFILM Business Innovation Corp., Tokyo (JP)

(72) Inventors: Shu Watanabe, Kanagawa (JP); Kunichi Yamashita, Kanagawa (JP); Kengo Tokuchi, Kanagawa (JP); Masamichi Kimura, Kanagawa (JP); Kota Nakayama, Kanagawa (JP); Akihide Kawamura, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 940 days.

(21) Appl. No.: 17/337,441

(22) Filed: Jun. 3, 2021

(65) Prior Publication Data

US 2022/0047762 A1 Feb. 17, 2022

(30) Foreign Application Priority Data

Aug. 14, 2020 (JP) .................. 2020-137022
Nov. 27, 2020 (JP) .................. 2020-197540

(51) Int. Cl.
*G06Q 10/02* (2012.01)
*A61L 2/24* (2006.01)
*A61L 9/20* (2006.01)
*A61L 101/26* (2006.01)

(52) U.S. Cl.
CPC ............... *A61L 9/20* (2013.01); *A61L 2/24* (2013.01); *G06Q 10/02* (2013.01); *A61L 2101/26* (2020.08); *A61L 2202/25* (2013.01); *A61L 2209/111* (2013.01); *A61L 2209/212* (2013.01)

(58) Field of Classification Search
None
See application file for complete search history.

(56) References Cited

U.S. PATENT DOCUMENTS

| | | | |
|---|---|---|---|
| 9,265,678 B2 * | 2/2016 | Hill | A61L 2/10 |
| 9,700,641 B2 * | 7/2017 | Hawkins | F21V 29/70 |
| 9,955,318 B1 * | 4/2018 | Scheper | G06Q 10/02 |
| 11,586,172 B2 * | 2/2023 | Lobo Fenoglietto | G05B 19/4099 |
| 11,775,879 B2 | 10/2023 | Watanabe | |

(Continued)

FOREIGN PATENT DOCUMENTS

| | | |
|---|---|---|
| JP | H036303 | 1/1991 |
| JP | 2001293070 | 10/2001 |

(Continued)

OTHER PUBLICATIONS

"Office Action of Japan Counterpart Application", issued on Jul. 2, 2024, with English translation thereof, p. 1-p. 8.

*Primary Examiner* — Jason Lin
(74) *Attorney, Agent, or Firm* — JCIPRNET

(57) ABSTRACT

An information processing system includes a processor configured to: acquire reservation information, the reservation information being information about a reservation of a booth; and make a determination regarding an improvement of an air environment by an improvement mechanism that improves the air environment provided inside the booth, on a basis of the acquired reservation information.

6 Claims, 20 Drawing Sheets

(56) References Cited

U.S. PATENT DOCUMENTS

| | | | |
|---|---|---|---|
| 2013/0085609 A1* | 4/2013 | Barker | G05B 15/02 |
| | | | 700/276 |
| 2014/0044590 A1* | 2/2014 | Trapani | A61L 2/10 |
| | | | 422/3 |
| 2016/0019813 A1* | 1/2016 | Mullen | G16H 15/00 |
| | | | 434/236 |
| 2017/0049915 A1* | 2/2017 | Brais | H05B 47/115 |
| 2018/0017947 A1* | 1/2018 | Kupa | G05B 13/021 |
| 2018/0299846 A1* | 10/2018 | Ray | H04L 41/0886 |
| 2019/0130317 A1* | 5/2019 | Watanabe | G06Q 10/02 |
| 2020/0009280 A1* | 1/2020 | Kupa | A61L 2/10 |
| 2020/0064790 A1* | 2/2020 | Galvez | G06Q 50/163 |
| 2021/0015959 A1 | 1/2021 | Goseki et al. | |
| 2022/0180460 A1 | 6/2022 | Ishida | |

FOREIGN PATENT DOCUMENTS

| | | |
|---|---|---|
| JP | 2003325651 | 11/2003 |
| JP | 2004097464 | 4/2004 |
| JP | 2005143706 | 6/2005 |
| JP | 2005201586 | 7/2005 |
| JP | 2005342142 | 12/2005 |
| JP | 2005342509 | 12/2005 |
| JP | 2006223634 | 8/2006 |
| JP | 2011045810 | 3/2011 |
| JP | 4691004 | 6/2011 |
| JP | 2011143378 | 7/2011 |
| JP | 2017136191 | 8/2017 |
| JP | 6490318 | 3/2019 |
| JP | 2019079406 | 5/2019 |
| JP | 2019082290 | 5/2019 |
| JP | 6607623 | 11/2019 |
| JP | 6687214 | 4/2020 |

* cited by examiner

FIG. 9

| | 4/4 | | 4/5 | | 4/6 | |
|---|---|---|---|---|---|---|
| | 4/4<br>06:00<br>\|<br>06:30 | ..... | 4/5<br>06:00<br>\|<br>06:30 | ..... | 4/6<br>06:00<br>\|<br>06:30 | ..... |
| | 4/4<br>06:30<br>\|<br>07:00 | ..... | 4/5<br>06:30<br>\|<br>07:00 | ..... | 4/6<br>06:30<br>\|<br>07:00 | ..... |
| | 4/4<br>07:00<br>\|<br>07:30 | ..... | 4/5<br>07:00<br>\|<br>07:30 | USER F | 4/6<br>07:00<br>\|<br>07:30 | ..... |
| | 4/4<br>07:30<br>\|<br>08:00 | ..... | 4/5<br>07:30<br>\|<br>08:00 | ..... | 4/6<br>07:30<br>\|<br>08:00 | ..... |
| | 4/4<br>08:00<br>\|<br>08:30 | ..... | 4/5<br>08:00<br>\|<br>08:30 | ..... | 4/6<br>08:00<br>\|<br>08:30 | ..... |
| | ..... | ..... | ..... | ..... | ..... | ..... |

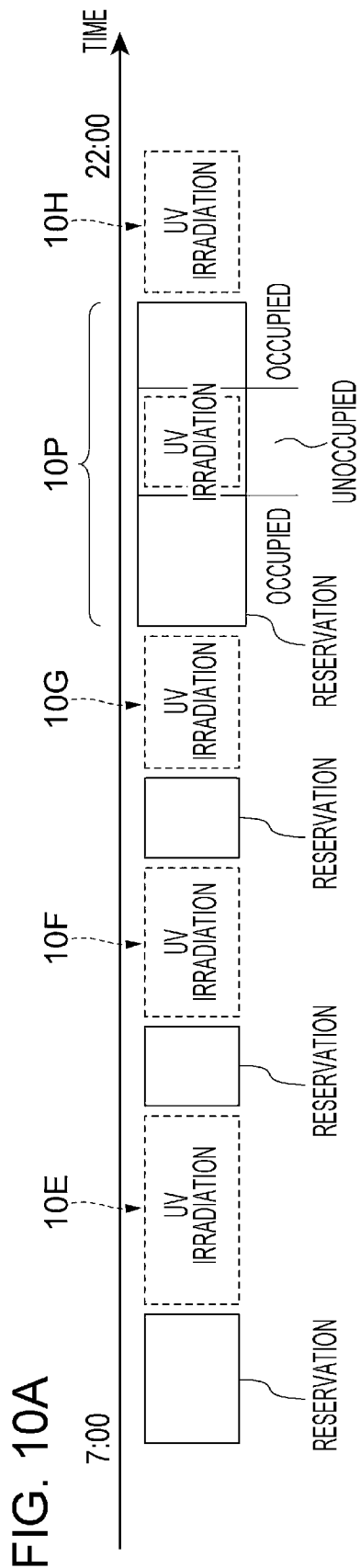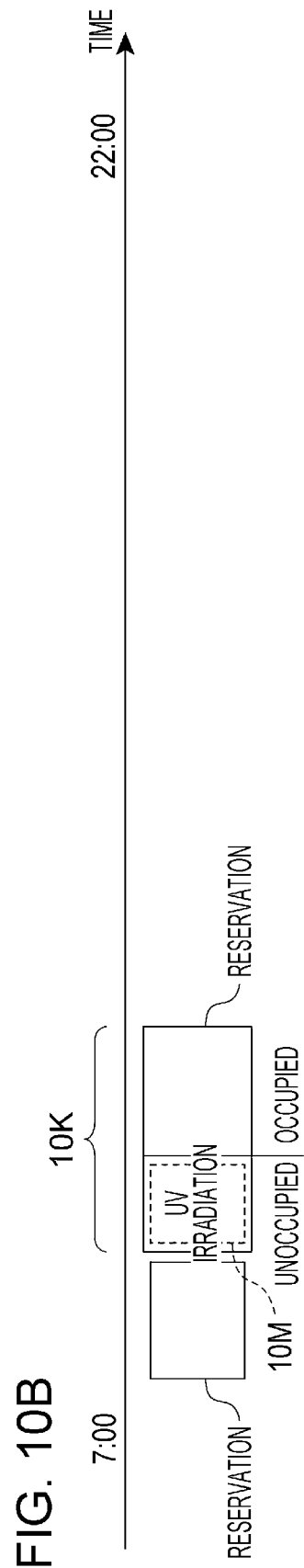

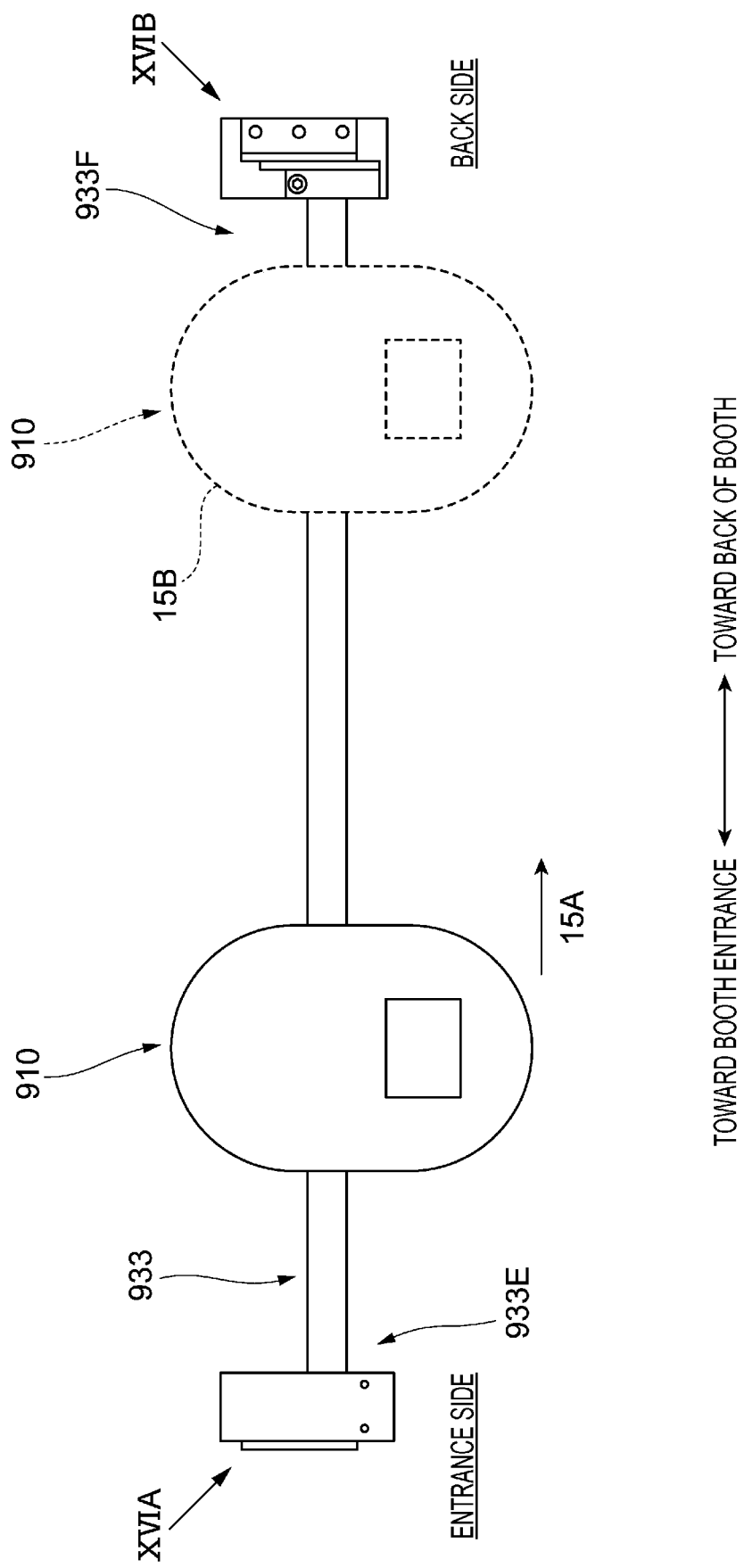

INFORMATION PROCESSING SYSTEM, NON-TRANSITORY COMPUTER READABLE MEDIUM, AND BOOTH

CROSS-REFERENCE TO RELATED APPLICATIONS

This application is based on and claims priority under 35 USC 119 from Japanese Patent Application No. 2020-137022 filed Aug. 14, 2020 and Japanese Patent Application No. 2020-197540 filed Nov. 27, 2020.

BACKGROUND

(i) Technical Field

The present disclosure relates to an information processing system, a non-transitory computer readable medium, and a booth.

(ii) Related Art

Japanese Unexamined Patent Application Publication No. 2005-342509 discloses a configuration in which a pre-filter having a deodorant function is provided on an air intake side and a deodorant filter is provided on an air exhaust side in a casing, while in addition, a special ultraviolet emitter and an ultraviolet emitter are disposed between the pre-filter and the deodorant filter in the casing.

SUMMARY

When cleaning a booth, if cleaning is performed at certain times on a fixed schedule, for example, the booth may be cleaned frequently even though the booth is not being used, or conversely the booth may not be cleaned even though the booth is being used frequently. Additionally, if cleaning is performed inside a reservation period of the booth, for example, there are concerns that cleaning may be performed while a user is inside the booth.

Aspects of non-limiting embodiments of the present disclosure relate to improving the air environment in a booth with consideration for the usage status of the booth.

Aspects of certain non-limiting embodiments of the present disclosure address the features discussed above and/or other features not described above. However, aspects of the non-limiting embodiments are not required to address the above features, and aspects of the non-limiting embodiments of the present disclosure may not address features described above.

According to an aspect of the present disclosure, there is provided an information processing system including a processor configured to: acquire reservation information, the reservation information being information about a reservation of a booth; and make a determination regarding an improvement of an air environment by an improvement mechanism that improves the air environment provided inside the booth, on a basis of the acquired reservation information.

BRIEF DESCRIPTION OF THE DRAWINGS

Exemplary embodiments of the present disclosure will be described in detail based on the following figures, wherein:

FIG. 9 is a diagram illustrating a reservation list stored in a hard disk drive of the space management server, and illustrates a reservation list for a booth reserved by a user;

FIGS. 10A and 10B are diagrams for explaining an example of processes performed by a CPU as an example of a processor;

FIG. 15 is a diagram of a case of viewing a support member and the light source from the direction indicated by the arrow XV in FIG. 14;

DETAILED DESCRIPTION

Hereinafter, exemplary embodiments of the present disclosure will be described with reference to the drawings.

Figure 1:
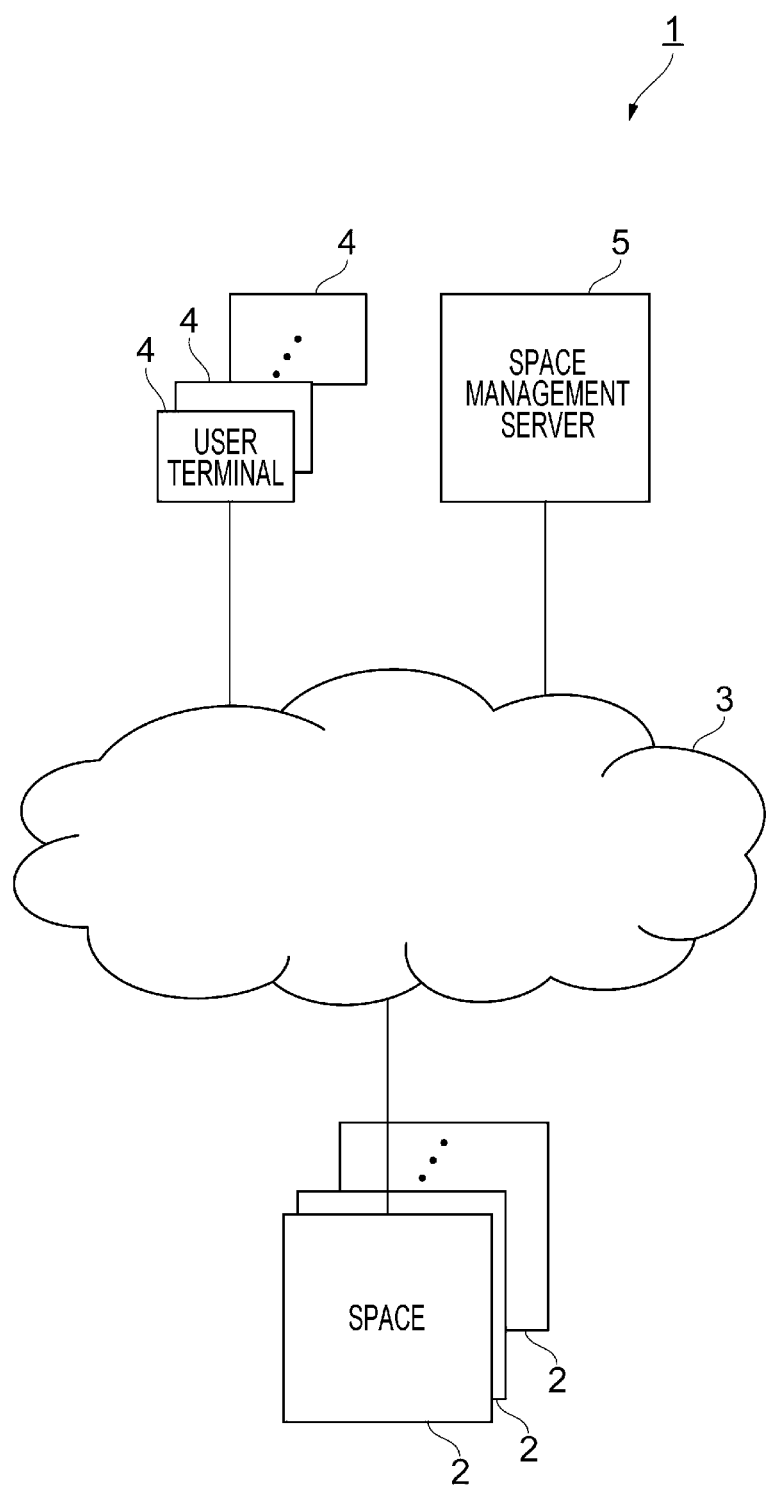
FIG. 1 is a diagram schematically illustrating an overall configuration of an information processing system.

FIG. 1 is a diagram schematically illustrating an overall configuration of an information processing system 1 according to the exemplary embodiment.

In the exemplary embodiment, a plurality of spaces 2 are provided as an example of places that are reserved for use by users.

In the exemplary embodiment, each of the spaces 2 is reservable, and a user is able to use a certain space 2 by reserving the space 2 in advance.

The spaces 2 may be booths, guest rooms in a lodging facility, conference rooms in a company office, or the like. These are examples of spaces 2 that are divided from the surroundings by walls, partitions, or the like.

Also, the spaces 2 in the exemplary embodiment include spaces such as tables or seats for receiving services provided at a facility such as a restaurant or a barber shop. These are examples of spaces 2 that are open to the surroundings.

The information processing system 1 illustrated in FIG. 1 includes various terminals connected to a cloud network 3.

Figure 3:
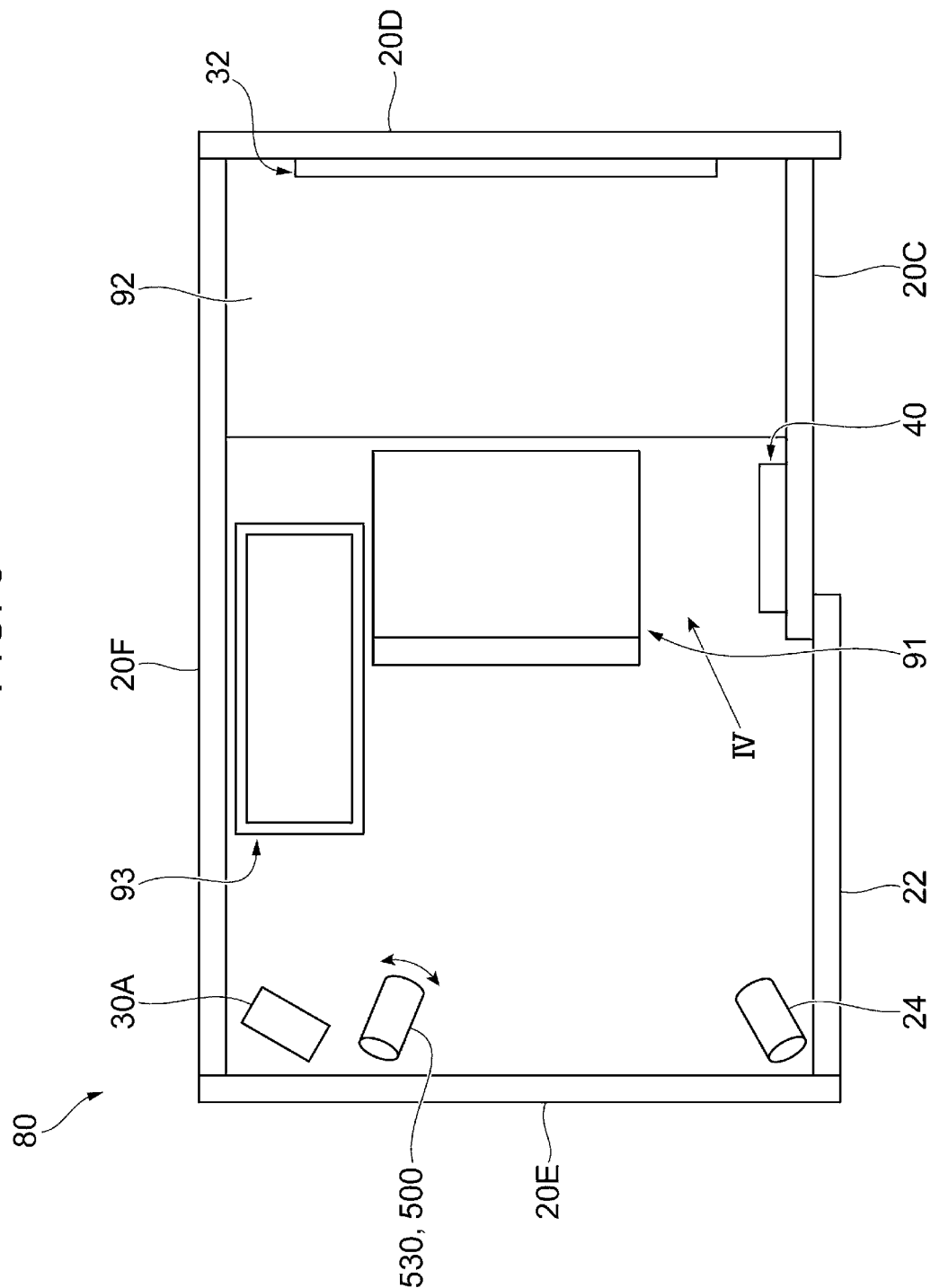
FIG. 3 is a diagram for explaining the interior of the booth.

In FIG. 3, user terminals 4 operated by users and a space management server 5 that manages the spaces 2 are illustrated as examples of the terminals connected to the cloud network 3. The spaces 2 are also connected to the cloud network 3. More specifically, various equipment is provided in the spaces 2, and the equipment is connected to the cloud network 3.

In the exemplary embodiment, the doors of the spaces 2 are fitted with an electronic lock, and each space 2 is lockable. In the exemplary embodiment, a person who has an unlocking right for a certain space 2 is able to use the space 2.

To unlock the space 2, the unlocking person operates his or her own user terminal 4 to give an unlock instruction. The instruction is transmitted to the space management server 5, and the space management server 5 receives the instruction. Thereafter, the space management server 5 issues an instruction to unlock the space 2 specified by the unlock instruction. With this arrangement, the electronic lock installed in the space 2 is activated, and the space 2 is unlocked.

In the exemplary embodiment, a portable smartphone is anticipated as the user terminal 4. However, the portable user terminal 4 may also be what is called a wearable terminal, and may also be a laptop computer or a game console.

The space management server 5 manages various information related to the spaces 2. The space management server 5 manages information that specifies users, information that specifies the spaces 2 available for reservation, the start dates and times of reservations, and the end dates and times of reservations, for example.

The information that specifies users includes the name, gender, and age of each user, an account, a user ID, a password, and individually-assigned management information for each user. Also, the information that specifies the spaces 2 available for reservation includes information that specifies the address or space where each space 2 is located for example, and a name or number used for management.

In addition, the space management server 5 also functions as a control device that controls the various equipment installed in the spaces 2.

Note that a control device may also be installed in each space 2 in correspondence with each of the spaces 2. In this case, the control device installed in each space 2 controls the various equipment installed in each space 2.

Exterior Configuration of Space 2

Figure 2:
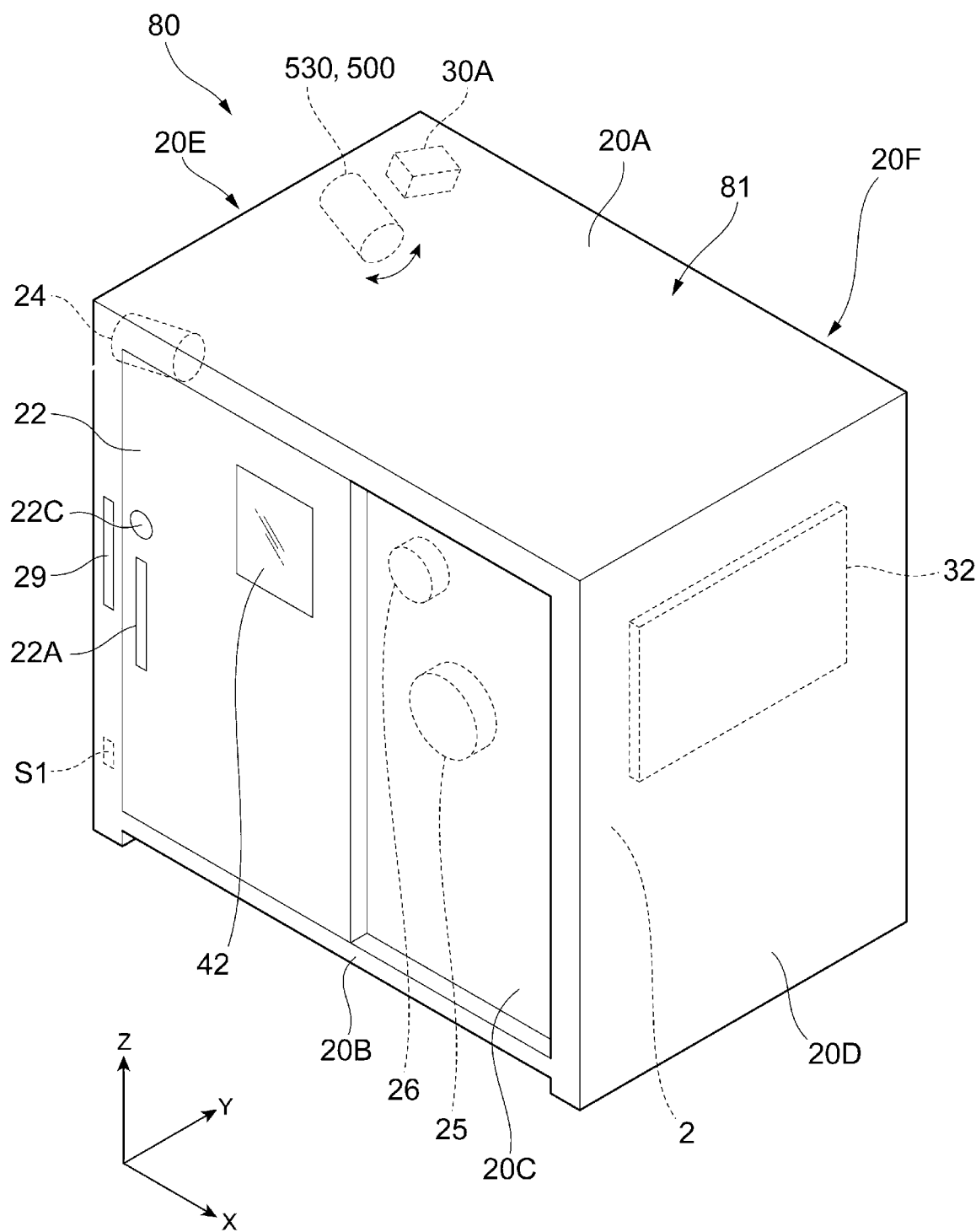
FIG. 2 is a diagram illustrating a booth.

FIG. 2 is a diagram illustrating a booth 80.

In the example illustrated in FIG. 2, the interior of the booth 80 is the space 2, and in the exemplary embodiment, the space 2 in the interior of the booth 80 is available for reservation.

The booth 80 in the exemplary embodiment is installed indoors or outdoors in any of various locations, including inside a train or subway station, an airport, an office building, a commercial facility such as a restaurant or a department store, a bank, a library, an art gallery, a museum, a public institution or facility, a passageway, or a park.

The booth 80 illustrated in FIG. 2 is an enclosed booth 80 with a ceiling.

Here, "enclosed" does not mean sealed, but refers to a state that achieves a practical level of soundproofing.

Also, the "booth 80" refers to a structure having partitions that partition the space 2 from other spaces positioned around the space 2. Here, the partitions do not necessarily exist on all four sides of the space 2, and even a structure that partially lacks partitions may still correspond to the booth 80.

For example, a configuration in which a user sits in and uses the space 2, and partitions exist only on the two sides to the left and the right of the user, may still correspond to the booth 80.

Furthermore, the ceiling does not have to be provided, and even a structure that lacks a ceiling may still correspond to the booth 80.

The booth 80 illustrated in FIG. 2 is provided with a frame 81 that forms a major part of the booth 80. The frame 81 is formed in a cuboid shape.

The booth 80 is provided with a ceiling 20A, a floor 20B, a wall 20C having an openable door 22 attached, two walls 20D and 20E positioned on either side of the wall 20C, and a wall 20F positioned on the opposite side from the door 22.

In the exemplary embodiment, the space 2 is surrounded by the wall 20C, the door 22, the wall 20D, the wall 20E, and the wall 20F, such that the space 2 is provided on the inner side of the four walls and the door 22.

In other words, in the exemplary embodiment, the space 2 is provided on the inner side of the frame 81.

In the exemplary embodiment, the door 22 is anticipated to be a sliding door that is movable parallel to the wall 20C. In the case of FIG. 2, the door 22 is a single sliding door 22 that slides in one direction, but the door 22 may also be a bypass door 22 that opens by sliding two or more panels past each other, or a double-sliding door 22 in which two panels slide away from each other.

A handle 22A that the user grasps when opening and closing the door 22 is attached to the door 22. Note that the handle may also be provided on the inner side of the door 22.

Additionally, an electronic lock 22C capable of locking and unlocking the door 22 is attached to the door 22. Furthermore, in the exemplary embodiment, an open/close sensor S1 that detects the opening and closing of the door 22 is provided.

The number of persons able to use the booth 80 is roughly determined according to the volume of the booth 80. The booth 80 in the exemplary embodiment is basically anticipated to be a personal space used by a single person. However, the booth 80 may also be a large booth 80 capable of accommodating many people.

Note that a personal space does not mean a space that is usable only by a single person, but is instead used to refer to a space usable by a small number of people, such as two to three people for example.

Furthermore, the frame 81 forming the booth 80 may have any shape or structure, and the equipment provided in the booth 80 may be of any type and capability.

FIG. 3 is a diagram for explaining the interior of the booth 80. Note that FIG. 3 illustrates a state of looking at the booth 80 from above.

In the exemplary embodiment, a desk 92 and a chair 91 are placed inside the booth 80.

A baggage container 93 into which the user places his or her belongings is also installed inside the booth 80. In other words, a baggage container 93 that holds the user's belongings that have been placed therein is provided inside the booth 80.

Also, a monitor 32, which is a display device for displaying video, is provided as furnished equipment inside the booth 80, as illustrated in FIGS. 2 and 3.

Also, a speaker 30A, which is a sound output device that outputs sound, is provided in the exemplary embodiment, as illustrated in FIGS. 2 and 3. Note that the speaker 30A does not have to be provided separately, and sound may also be output from a speaker built into the monitor 32.

Also, in the exemplary embodiment, an imaging device 24 that takes images of the interior of the booth 80 is provided, as illustrated in FIGS. 2 and 3. The imaging device 24 is provided with an image sensor such as a CCD or CMOS sensor. The imaging device 24 uses the image sensor to take an image of the interior of the booth 80.

Also, as illustrated in FIG. 2, the booth 80 is provided with a human sensor 25 that detects the user or users inside the booth 80. Also, in the exemplary embodiment, a temperature sensor 26 that detects the temperature inside the booth 80 is provided.

Also, as illustrated in FIG. 3, lighting equipment 40 for lighting the interior of the booth 80 is provided inside the booth 80.

Furthermore, in the exemplary embodiment, a window 42 is installed in the door 22, as illustrated in FIG. 2. In the exemplary embodiment, the interior of the space 2 is visible through the window 42 from the outside of the space 2.

Furthermore, as illustrated in FIG. 2, an information acquisition device 29 for acquiring individual information about each user who uses the booth 80 may also be provided on the outer surface of the booth 80.

The information acquisition device 29 includes a reader that reads an ID card held up to the reader, for example. Otherwise, the information acquisition device 29 may be a reader or the like that acquires information such as a user's fingerprint or vein pattern.

Figure 4:
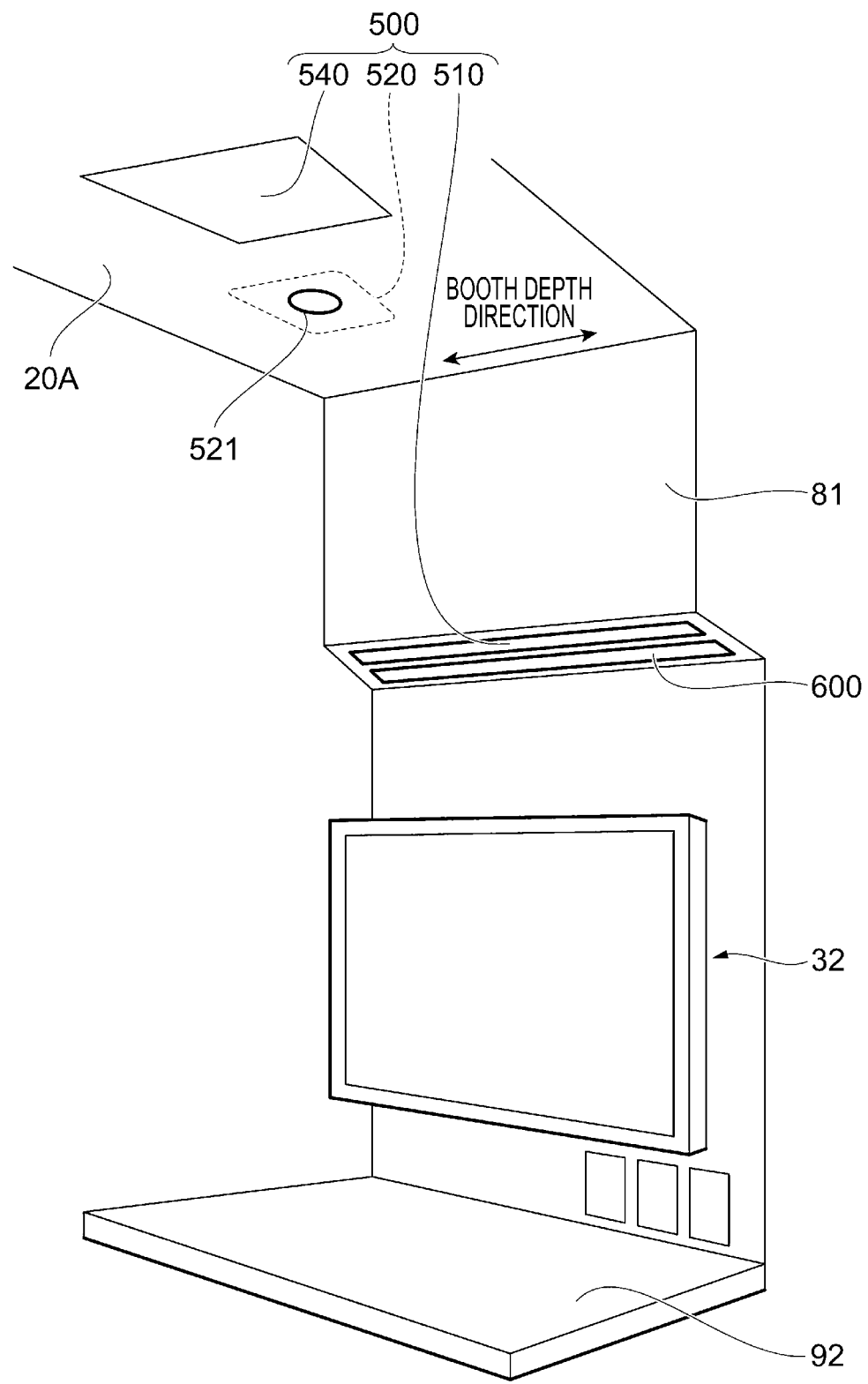
FIG. 4 is a diagram of a case of viewing the interior of the booth from the direction indicated by the arrow IV in FIG. 3.

FIG. 4 is a diagram of a case of viewing the interior of the booth 80 from the direction indicated by the arrow IV in FIG. 3.

In the exemplary embodiment, an improvement mechanism 500 is provided inside the booth 80 as an example of an improvement mechanism that improves the air environment inside the booth 80.

In other words, in the exemplary embodiment, the improvement mechanism 500 that improves the air environment inside the booth 80 is provided in the interior of the frame 81 forming the booth 80.

In the exemplary embodiment, a light source 510 that emits ultraviolet light containing ultraviolet rays, a spraying device 520 that emits a liquid in a spray, and a ceiling light source 540 that is attached to the ceiling 20A of the booth 80 and that emits ultraviolet light likewise containing ultraviolet rays are provided as the improvement mechanism 500.

In the exemplary embodiment, the ceiling light source 540 is used to irradiate the entire interior of the booth 80 with ultraviolet light. Also, the light source 510 is installed in a location closer to the desk 92 than the ceiling light source 540, and mostly radiates ultraviolet light toward the desk 92.

In the exemplary embodiment, by providing not only the ceiling light source 540 but also the light source 510, surfaces frequently touched by the user of the booth 80 such as the top of the desk 92 and installed objects such as a keyboard placed on top of the desk 92 may be irradiated with ultraviolet light from a short distance away and with high intensity.

Note that radiating ultraviolet light from a spot closer than the ceiling 20A, such as radiating ultraviolet light onto the desk 92 from the light source 510, may lead to increased deterioration and fading of the desk 92 and installed objects placed on the desk 92 compared to the case of radiating ultraviolet light from the ceiling 20A. More specifically, ultraviolet light of lower wavelengths lead to increased deterioration and fading of the desk 92 and installed objects.

Consequently, when radiating ultraviolet light, a process that turns on only the ceiling light source 540 during time periods such as at night (when the ultraviolet light radiation time is longer than a predetermined threshold) is conceivable as an example.

Also, when radiating ultraviolet light, a process that turns on only the light source 510 or both the light source 510 and the ceiling light source 540 may be performed in situations where it is difficult to secure the radiation time, such as during breaks between reservation periods (when the ultraviolet light radiation time is shorter than the above predetermined threshold).

The improvement mechanism 500 according to the exemplary embodiment improves the air environment in the interior of the frame 81 by emitting ultraviolet light from the ceiling light source 540 and the light source 510 to irradiate the interior of the frame 81 with ultraviolet light. Additionally, the improvement mechanism 500 improves the air environment in the interior of the frame 81 by activating the spraying device 520 to spray the interior of the frame 81 with a mist of liquid.

Here, the light source 510 is disposed along the depth direction of the booth 80. Also, in the exemplary embodiment, a light source 600 for illumination that emits visible light is provided beside the light source 510 that emits ultraviolet light.

The spraying device 520 is installed in the ceiling 20A of the booth 80, and the ceiling 20A is provided with an outlet 521 from which the mist of liquid generated by the spraying device 520 is discharged. The improvement mechanism 500 improves the air environment in the interior of the frame 81 by using the spraying device 520 to discharge a mist of liquid from the outlet 521.

Also, in the exemplary embodiment, as illustrated in FIGS. 2 and 3, a light source 530 of a movable type (hereinafter, the "movable light source 530") is provided as the improvement mechanism 500.

The movable light source 530 also emits ultraviolet light. Furthermore, in the exemplary embodiment, a light source driving mechanism (not illustrated) that changes the attitude of the movable light source 530 is provided.

The light source driving mechanism is not particularly limited, and may have a known configuration including a motor or the like.

In the exemplary embodiment, the light source driving mechanism is driven and the attitude of the movable light source 530 is changed according to an instruction from the space management server 5. With this arrangement, multiple spots inside the frame 81 may be irradiated with ultraviolet light.

Here, in the exemplary embodiment, the movable light source 530 ordinarily is pointed toward the chair 91 (see FIG. 3) and the desk 92.

Note that although the case of improving the air environment by emitting ultraviolet light and spraying a liquid is described as an example in the exemplary embodiment, the ways of improving the air environment are not limited to the above.

For example, the air environment inside the booth 80 may also be improved by causing a mobile cleaning machine that moves autonomously to move inside the booth 80.

As another example, air may be blown onto each area inside the booth 80 to kick up dust adhering to each area, while in addition, the booth 80 may be ventilated to exhaust the dust-containing air to the outside of the booth 80.

Here, in the exemplary embodiment, the spraying device 520 sprays a liquid containing titanium oxide. Next, in the exemplary embodiment, ultraviolet light is emitted from one or more light sources among the light source 510, the movable light source 530, and the ceiling light source 540, and ultraviolet light is radiated onto each area including spots where the titanium oxide adheres. With this arrangement, contaminants that contaminate the air inside the booth 80 are reduced, and the air environment of the booth 80 is improved.

Here, in the improvement mechanism 500 according to the exemplary embodiment, the two types of processes of spraying a liquid and radiating ultraviolet light may be performed, but in the exemplary embodiment, multiple types of processes may be performed.

Note that to improve the air environment, both spraying a liquid and radiating ultraviolet light do not necessarily have to be performed, and as described later, only radiating ultraviolet light may be performed.

Also, the liquid sprayed from the spraying device 520 is not limited to a liquid containing titanium oxide, may also be a liquid containing a chemical solution.

Additionally, the liquid sprayed from the spraying device 520 may also be a liquid containing a material based on tungsten oxide (WO3). In this case, the air environment may be improved by radiating visible light (having a wavelength of 400 nm or higher) onto spots where the liquid adheres.

In other words, in the case of improving the air environment by spraying a liquid containing titanium oxide, ultraviolet light radiation is used, but in the case of spraying a liquid containing a material based on tungsten oxide, the air environment may be improved by radiating visible light.

A material based on tungsten oxide (WO3) is produced by doping titanium oxide with nitrogen or the like, or by the ion implantation of dissimilar metals.

Examples of materials based on tungsten oxide (WO3) include the following.
(1) Copper compound modified tungsten oxide photocatalyst
(2) Copper compound modified titanium oxide photocatalyst
(3) Iron compound modified titanium oxide photocatalyst Also, in the exemplary embodiment, the spots irradiated with ultraviolet light may be changed.

Specifically, in the exemplary embodiment, the attitude of the movable light source 530 may be changed as described above, and therefore by changing the attitude of the movable light source 530, the spots irradiated with ultraviolet light may be changed.

More specifically, the spots irradiated with ultraviolet light are changed by driving the light source driving mechanism (not illustrated).

Here, in the exemplary embodiment, the improvement mechanism 500 is activated and the air environment is improved by the improvement mechanism 500 according to an instruction from the space management server 5.

Furthermore, in the exemplary embodiment, the air environment is also improved by the improvement mechanism 500 in the case of receiving an instruction from the terminal device carried by the user of the booth 80, namely the user terminal 4, or from a terminal device carried by cleaning personnel. In other words, in the exemplary embodiment, the air environment is also improved by the improvement mechanism 500 in the case of receiving an instruction from a mobile terminal carried by a person.

More specifically, in the exemplary embodiment, if cleaning personnel or the user of the booth 80 operates a terminal device to give an instruction to improve the air environment, the instruction is transmitted to the space management server 5. Thereafter, in this case, the space management server 5 outputs an instruction to start improving the air environment. With this arrangement, the improvement mechanism 500 is activated and the air environment inside the booth 80 is improved.

Also, in the exemplary embodiment, as described later, the space management server 5 makes a determination about improving the air environment of the booth 80 on the basis of reservation information, which is information about reservations of the booth 80. Additionally, in the exemplary embodiment, the air environment is improved by the improvement mechanism 500 on the basis of the determination.

Note that in the exemplary embodiment, a hardware switch for receiving an instruction to start the improvement of the air environment by the improvement mechanism 500 is not provided on either the inside or the outside the booth 80.

In other words, in the exemplary embodiment, a reception unit touchable by the user of the booth 80 for receiving an instruction to start the improvement of the air environment by the improvement mechanism 500 is not provided on either the inside or the outside of the booth 80.

In this case, there is a reduction in situations where the improvement of the air environment is performed because the user of the booth 80 accidentally touches a switch for improving the air environment inside the booth 80. More specifically, accidental spraying of liquid and accidental emission of ultraviolet light are reduced.

Figure 5:
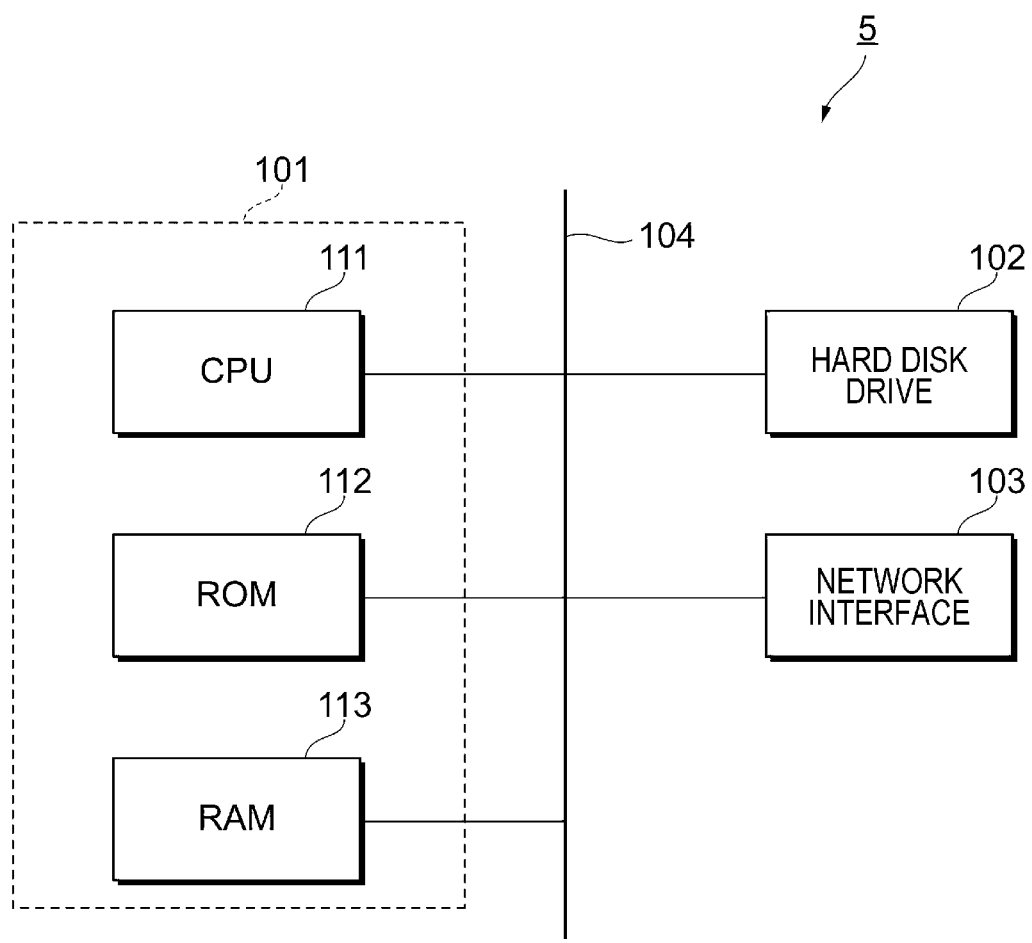
FIG. 5 is a diagram for explaining an example of a hardware configuration of a space management server.

FIG. 5 is a diagram for explaining an example of a hardware configuration of the space management server 5.

The space management server 5 acts as one example of an information processing device, and includes a control unit 101 that controls the operations of the overall device, a hard disk drive 102 that stores management data and the like, and a network interface 103 that achieves communication through a local area network (LAN) cable or the like.

The control unit 101 includes a central processing unit (CPU) 111 as one example of a processor, read-only memory (ROM) 112 storing data such as low-level software and a basic input-output system (BIOS), and random access memory (RAM) 113 that is used as a work area.

The CPU 111 may also be multi-core. Additionally, the ROM 112 may be rewritable non-volatile semiconductor memory. The control unit 101 may also be referred to as a computer.

The hard disk drive 102 is a device that reads and writes data with respect to a non-volatile storage medium in which the surface of a disk-shaped substrate is coated with a magnetic substance. Obviously, the non-volatile storage medium may also be semiconductor memory or magnetic tape.

Besides the above, the space management server 5 is also provided with an input device such as a keyboard or mouse and a display device such as a liquid crystal display as appropriate.

The control unit 101, the hard disk drive 102, and the network interface 103 are connected by a bus 104 and through signal lines not illustrated.

Here, a program executed by the CPU 111 may be provided to the space management server 5 in a recorded state on a computer-readable recording medium, such as a magnetic recording medium (such as magnetic tape or a magnetic disk), an optical recording medium (such as an optical disc), a magneto-optical recording medium, or semiconductor memory. Additionally, a program executed by the CPU 111 may also be provided to the space management server 5 using a communication medium such as the Internet.

Note that in the exemplary embodiment, the term "processor" refers to hardware in a broad sense. Examples of the processor include general processors (e.g., CPU: Central Processing Unit), dedicated processors (e.g., GPU: Graphics Processing Unit, ASIC: Application Integrated Circuit, FPGA: Field Programmable Gate Array, and programmable logic device).

Also, the term "processor" is broad enough to encompass one processor or plural processors in collaboration which are located physically apart from each other but may work cooperatively. The order of operations of the processor is not limited to one described in the exemplary embodiment, and may be changed.

Figure 6:
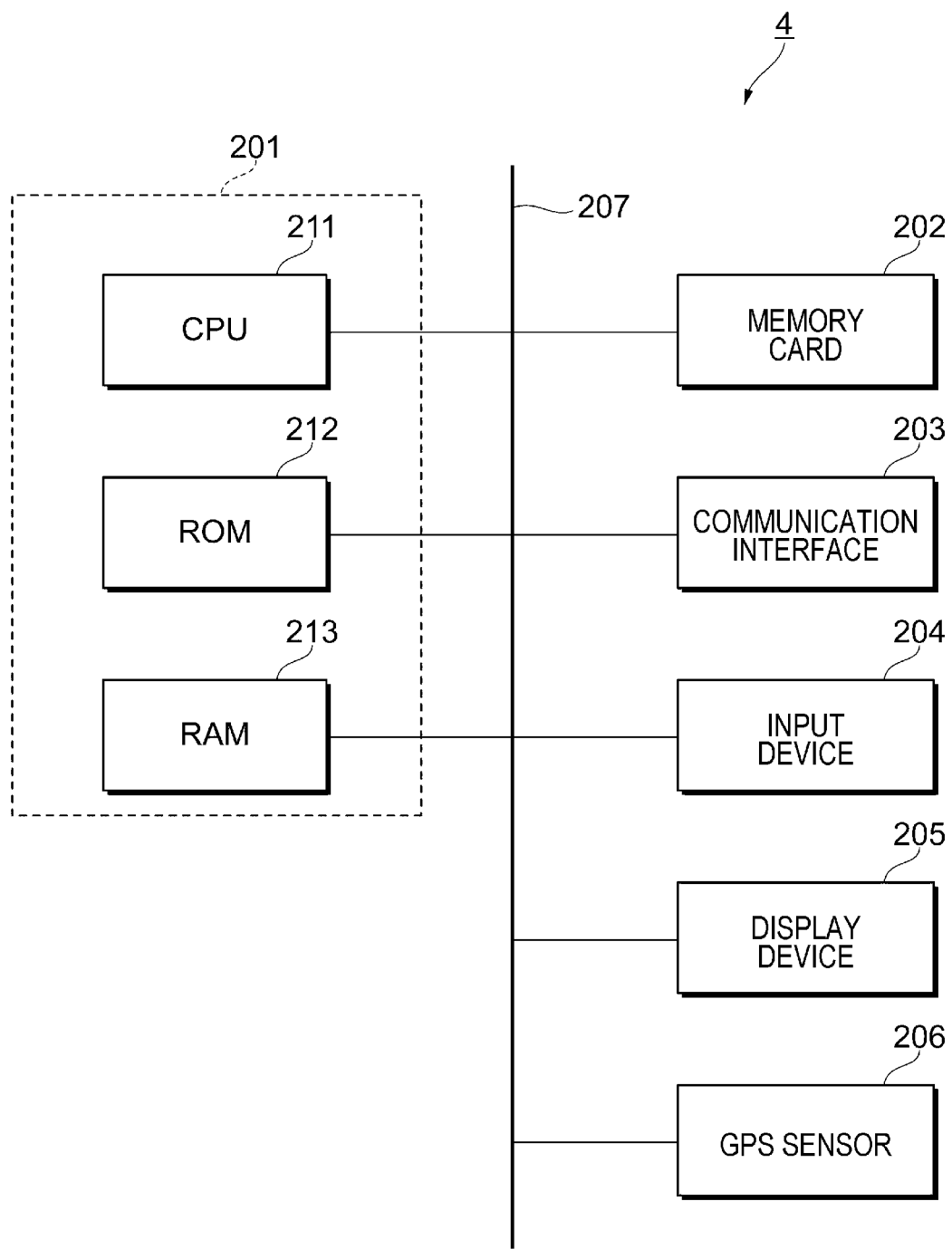
FIG. 6 is a diagram illustrating an example of a hardware configuration of a user terminal.

FIG. 6 is a diagram illustrating an example of a hardware configuration of the user terminal 4. The configuration illustrated in FIG. 6 anticipates the case where the user terminal 4 is a smartphone.

The user terminal 4 includes a control unit 201 that controls the operations of the overall device, a memory card 202 that stores various data, any of various types of communication interfaces 203 that conform to wireless communication standards, an input device 204 such as a touch sensor, a display device 205 such as a liquid crystal display or an organic electroluminescence (EL) display, and a Global Positioning System (GPS) sensor 206.

The control unit 201 includes a CPU 211, ROM 212 storing data such as firmware and a BIOS, and RAM 213 that is used as a work area. The CPU 211 may also be multi-core. Additionally, the ROM 212 may be rewritable non-volatile semiconductor memory.

The communication interfaces 203 include an interface used to connect to a mobile communication system and an interface used to connect to a wireless LAN, for example.

The GPS sensor 206 is a sensor that receives radio waves from GPS satellites to measure the position of the user terminal 4. Latitude, longitude, and altitude information output from the GPS sensor 206 gives the current position of the user terminal 4. Note that the GPS sensor 206 may also support a positioning system for indoor use.

Figure 7:
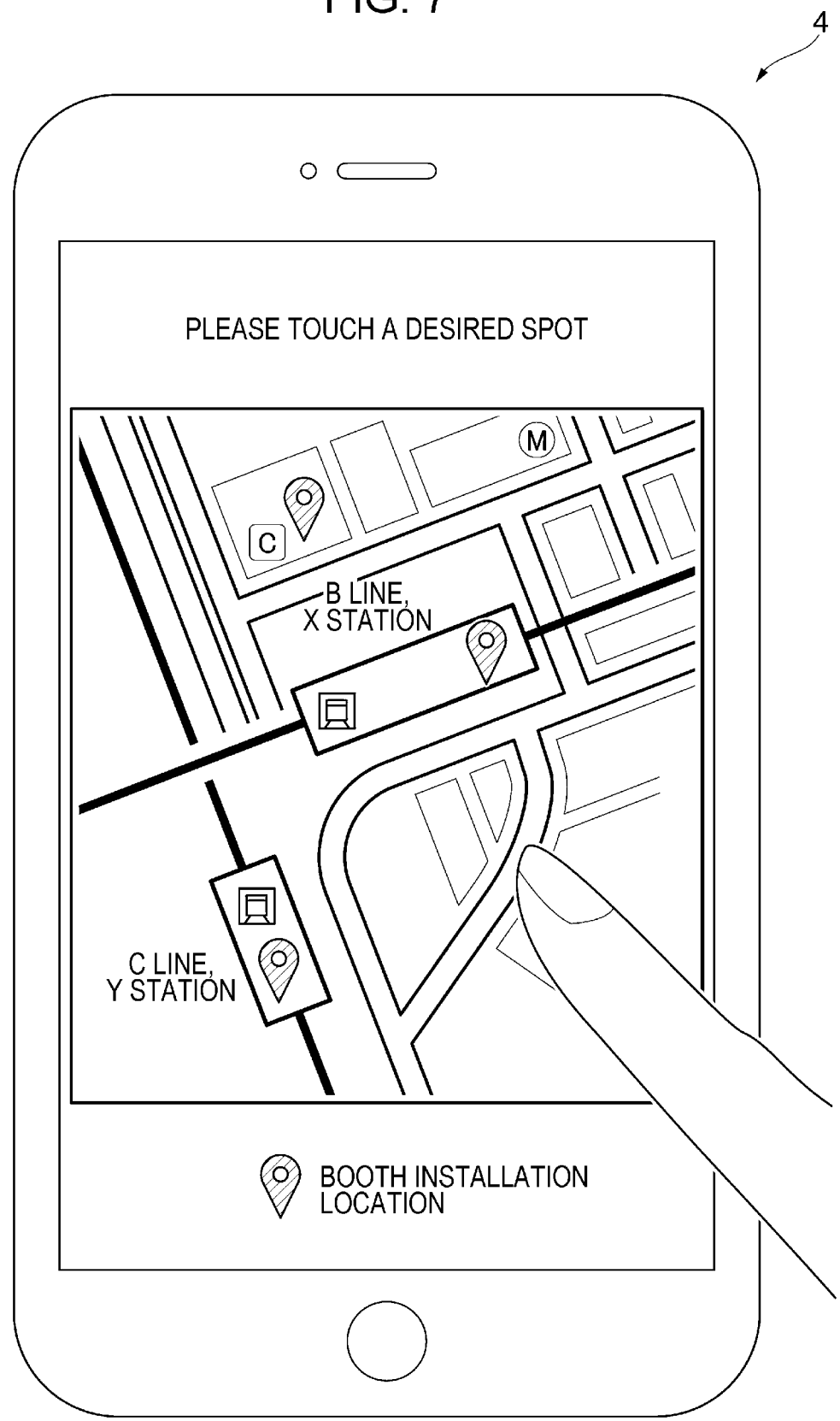
FIG. 7 is a diagram illustrating an example of a display screen displayed on the user terminal of a user of a booth when the user reserves a booth.
Figure 8:
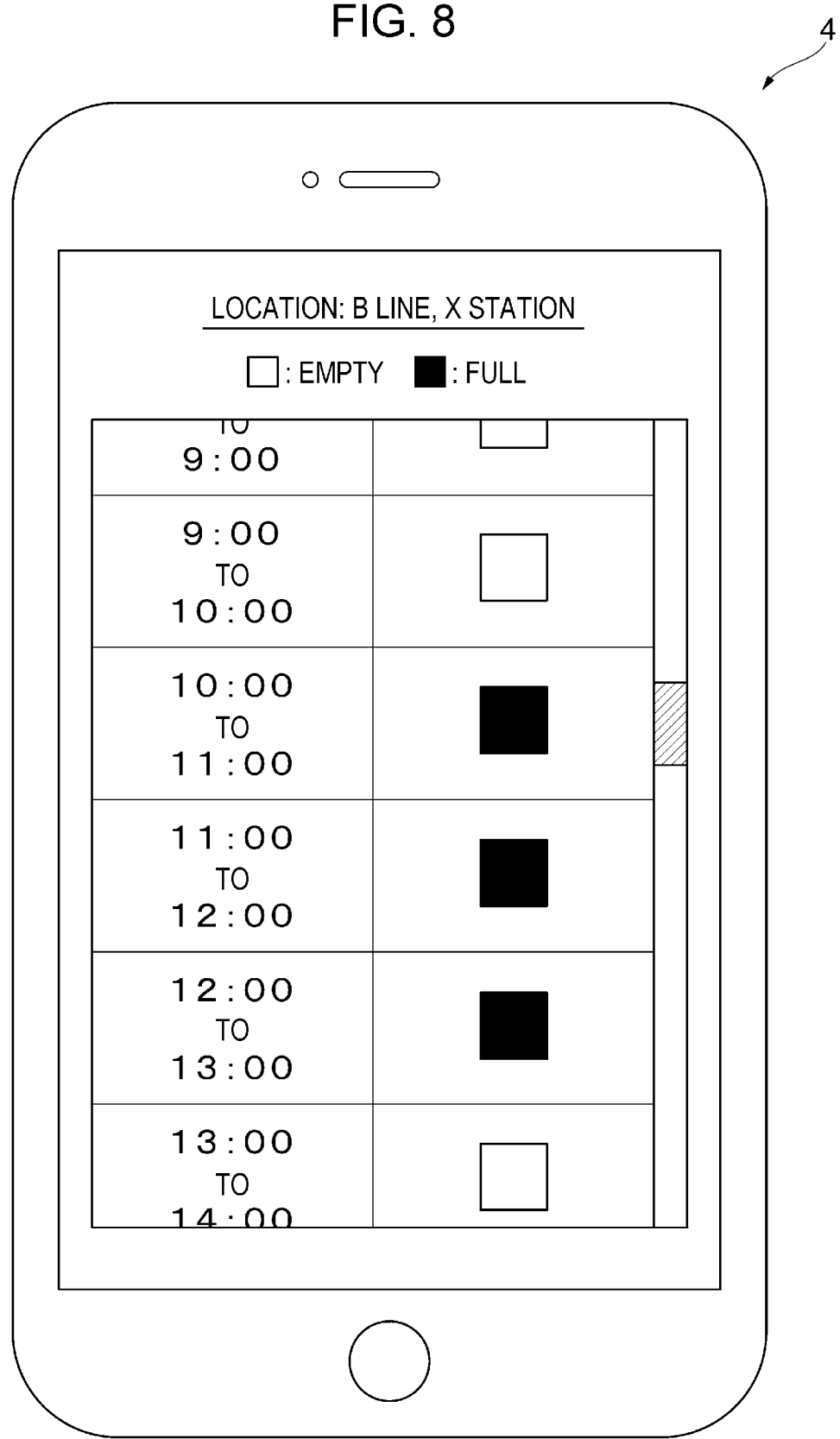
FIG. 8 is a diagram illustrating another example of a display screen displayed on the user terminal.

FIG. 7 is a diagram illustrating an example of a display screen displayed on the user terminal 4 of a user of a booth 80 when the user reserves the booth 80.

On the display screen illustrated in FIG. 7, a map is displayed, and multiple installation locations of the booths 80 are displayed on the map.

In the exemplary embodiment, when a user of a booth 80 reserves a booth 80, first, the user selects an installation location from among the multiple displayed installation locations.

Note that the display is not limited to such an appearance. For example, multiple installation locations may also be displayed in a list format, and the user may select an installation location from the list.

When an installation location is selected, the occupancy status at the selected installation location is displayed for individual time slots, as illustrated in Fig. (a diagram illustrating another example of a display screen displayed on the user terminal 4).

The user performs an operation on the display screen to specify a reservation period. Additionally, the user presses a confirmation button (not illustrated).

In response, the space management server 5 performs a reservation confirmation process.

Specifically, after receiving information about the installation location of the booth 80 and the reservation period, the space management server 5 registers information about the installation location and the reservation period in the hard disk drive 102 (FIG. 5), and performs a reservation confirmation process.

In other words, after receiving information about the installation location of the booth 80 and the reservation period, the space management server 5 registers information about the installation location and the reservation period in the hard disk drive 102 (FIG. 5), and performs a reservation confirmation process.

Thereafter, the reservation confirmation result is transmitted to the user terminal 4 to notify the user making the reservation.

FIG. 9 is a diagram illustrating a reservation list stored in the hard disk drive 102 of the space management server 5, and illustrates a reservation list for a booth 80 reserved by a user.

In the exemplary embodiment, when a reservation of a booth 80 by a user is confirmed, the user is added to the reservation list, as illustrated in FIG. 9. More specifically, the user who is the person making the reservation is registered in a reservation time period on the reservation list.

Furthermore, in the exemplary embodiment, information about reservations of the booth 80 (hereinafter referred to as "reservation information") is registered in the hard disk drive 102 of the space management server 5.

In the example illustrated in FIG. 9, information indicating that a user F has reserved the time of the reservation period from 07:00 to 07:30 on April 5th is registered as the reservation information.

Also, although a detailed description is omitted, information indicating reservations by users is registered similarly for other reservation periods.

FIGS. 10A and 10B are diagrams for explaining an example of processes performed by the CPU 111 (see FIG. 5) as an example of a processor. In other words, FIGS. 10A and 10B are diagrams for explaining processes performed by the CPU 111 provided in the space management server 5.

The CPU 111 according to the exemplary embodiment acquires the above reservation information, which is information about reservations of the booth 80, and on the basis of the acquired reservation information, makes a determination about the improvement of the air environment performed by the improvement mechanism 500 provided inside the booth 80.

In other words, the CPU 111 acquires the reservation information registered in the hard disk drive 102, and on the basis of the acquired reservation information, makes a determination about the improvement of the air environment by the improvement mechanism 500 provided inside the booth 80.

Specifically, on the basis of the acquired reservation information, the CPU 111 specifies a time period in which the booth 80 is not reserved, and determines to improve the air environment with the improvement mechanism 500 in the time period in which the booth 80 is not reserved.

In other words, the CPU 111 makes a determination about whether or not to cause the improvement mechanism 500 to execute the improvement of the air environment. In this determination, the CPU 111 specifies a time period in which the booth 80 is not reserved, on the basis of the acquired reservation information. The CPU 111 then determines to improve the air environment with the improvement mechanism 500 in the time period in which the booth 80 is not reserved.

With this arrangement, in the exemplary embodiment, the air environment is improved by the improvement mechanism 500 in a time period other than a reservation time period, which is a time period in which the booth 80 is reserved.

The example illustrated in FIG. 10A illustrates a case where multiple reservations have been made between 7:00 and 22:00.

When the CPU 111 determines to improve the air environment with the improvement mechanism 500 in a time period in which the booth 80 is not reserved, as illustrated in FIG. 10A, the air environment is improved by the improvement mechanism 500 in each of the time periods in which the booth 80 is not reserved.

More specifically, in the example illustrated in FIG. 10A, each of the time periods indicated by the signs 10E, 10F, 10G, and 10H is a time period in which the booth 80 is not reserved, and the air environment is improved by the improvement mechanism 500 in each of these time periods.

More specifically, in this case, every time one of the time periods indicated by the signs 10E, 10F, 10G, and 10H is reached, the CPU 111 outputs a control signal causing the improvement mechanism 500 to start the improvement of the air environment.

With this arrangement, in the exemplary embodiment, the air environment is improved by the improvement mechanism 500 in each of the time periods indicated by the signs 10E, 10F, 10G, and 10H.

Specifically, in this example, ultraviolet light is radiated from one or more light sources among the light source 510, the movable light source 530, and the ceiling light source 540, and the air environment inside the booth 80 is improved.

Note that although this example describes a case where ultraviolet light is radiated in a time period in which the booth 80 is not reserved, the configuration is not limited thereto, and ultraviolet light may be radiated in a time period in which the booth 80 is not reserved and also in the case where a person is not present inside the booth 80.

More specifically, it may be configured such that ultraviolet light is radiated in a time period in which the booth 80 is not reserved and the output from the human sensor 25 (see FIG. 2) indicates that a person is not present.

In other words, it may be configured such that ultraviolet light is not radiated in the case where a person is present inside the booth 80, even in a time in which the booth 80 is not reserved.

In other words, the determination regarding the radiation of ultraviolet light may be made on the basis of not only the reservation status of the booth 80, but also with consideration for whether or not a person is inside the booth 80.

Note that in the case of using ultraviolet light having a wavelength of 254 nm for example as the user, the effects on a user inside the booth 80 are large, and therefore it is preferable to radiate ultraviolet light in a time period in which the booth 80 is not reserved, or in a time period in which the booth 80 is not reserved and a person is not present inside the booth 80 as described above. In other words, in the case of using ultraviolet light having a wavelength of 254 nm, it is preferable to manage the radiation of ultraviolet light strictly.

In contrast, in the case of radiating ultraviolet light having a wavelength of 222 nm for example as the ultraviolet light, the effects on the human body are small, and ultraviolet light may be radiated at any time. In other words, in the case of radiating 222 nm ultraviolet light, the radiation of ultraviolet light may be performed in a time period in which the booth 80 is reserved or in situations where a person is present inside the booth 80. In other words, in the case of radiating 222 nm ultraviolet light, the radiation of ultraviolet light may be performed without strict management.

Otherwise, the CPU 111 according to the exemplary embodiment may determine to improve the air environment with the improvement mechanism 500 when a specific condition is satisfied, even in a reservation time period which is a time period in which the booth 80 is reserved, for example.

Specifically, the CPU 111 determines to improve the air environment with the improvement mechanism 500 even in a reservation period in the case where an instruction to improve the air environment is received from the user of the booth 80, for example.

Specifically, the time period indicated by the sign 10K in FIG. 10B is a reservation time period reserved by a user of the booth 80.

In the exemplary embodiment, even in a reservation period, in the case where an instruction to improve the air environment is received from the user of the booth 80, the CPU 111 determines to improve the air environment with the improvement mechanism 500.

More specifically, the CPU 111 determines to improve the air environment with the improvement mechanism 500 even in a reservation period in the case where the booth 80 is unoccupied and an instruction to improve the air environment is received from the user of the booth 80, for example.

More specifically, the CPU 111 determines to improve the air environment with the improvement mechanism 500 even in a reservation period in the case where the booth 80 is unoccupied and an instruction is received from the user terminal 4 carried by the user of the booth 80.

Note that the CPU 111 determines whether or not the booth 80 is unoccupied on the basis of the output from the human sensor 25 (see FIG. 2).

Figure 11:
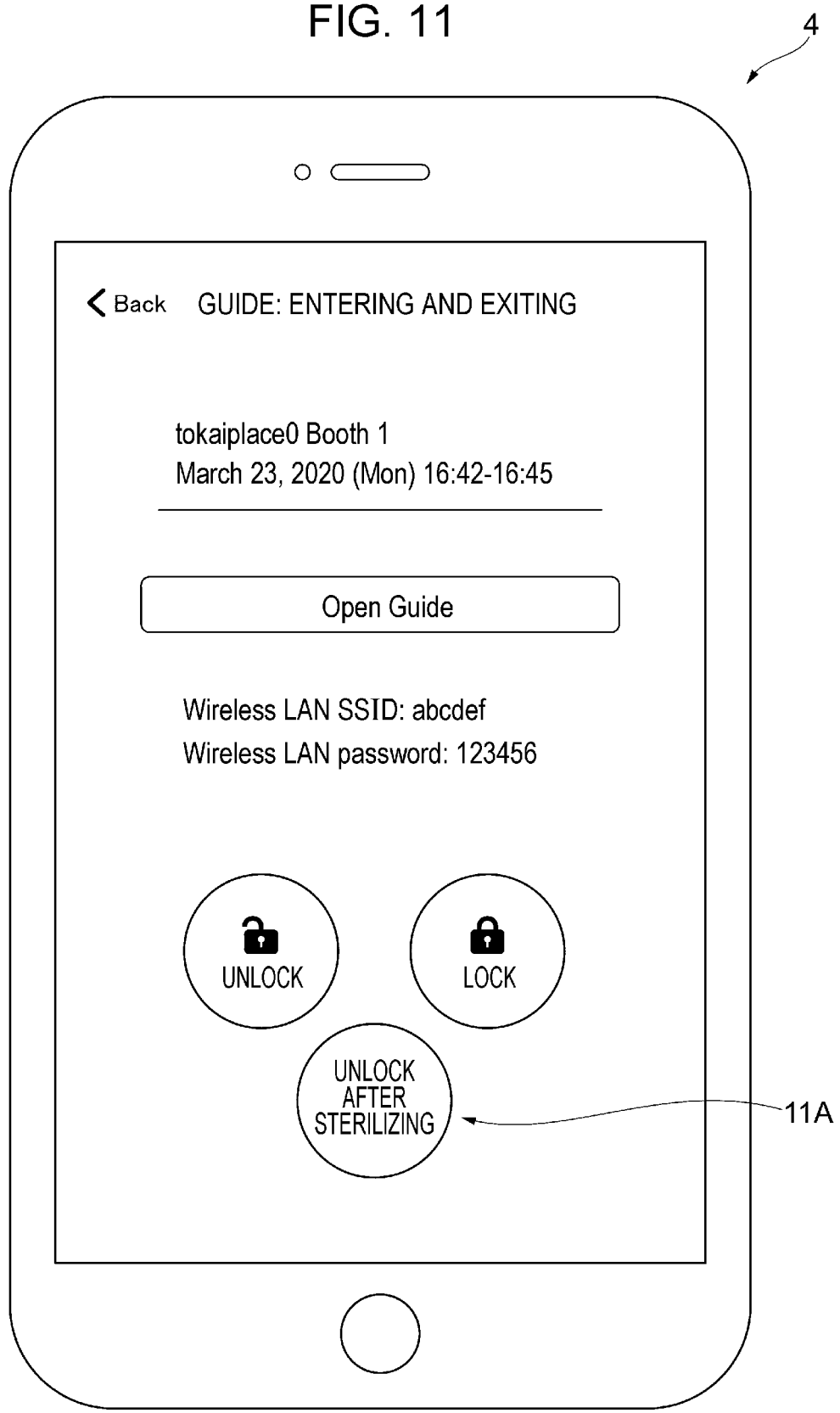
FIG. 11 is a diagram illustrating an example of a display screen displayed on the user terminal in the case where the user of the booth gives an instruction to improve the air environment.

FIG. 11 is a diagram illustrating an example of a display screen displayed on the user terminal 4 in the case where the user of the booth 80 gives an instruction to improve the air environment.

On the display screen of the user terminal 4 illustrated in FIG. 11, a button labeled "Unlock after sterilizing" is displayed, as indicated by the sign 11A. In the exemplary embodiment, the display screen illustrated in FIG. 11 is displayed on the 4 in the case where the user of the booth 80 gives an instruction to improve the air environment.

Additionally, in the exemplary embodiment, in the case where the button labeled "Unlock after sterilizing" is pressed by the user and the booth 80 is also unoccupied, the CPU 111 determines to improve the air environment with the improvement mechanism 500.

With this arrangement, in this case, as indicated by the sign 10M in FIG. 10B, ultraviolet light is radiated from one or more light sources among the light source 510, the movable light source 530, and the ceiling light source 540, and the interior of the booth 80 is irradiated with ultraviolet light. In this case, the air environment is improved by the improvement mechanism 500 before the user begins using the booth 80.

Thereafter, in this process example, the CPU 111 gives an instruction to unlock the booth 80. In other words, the CPU 111 gives an instruction to unlock the booth 80 after the improvement of the air environment of the booth 80 by the improvement mechanism 500 is finished.

In other words, the CPU 111 gives an instruction to unlock the booth 80 after the improvement of the air environment according to the instruction from the user of the booth 80 is finished and the light source 510, the movable light source 530, and the ceiling light source 540 are switched off.

With this arrangement, the electronic lock 22C (see FIG. 2) is activated and the booth 80 is unlocked. In this case, the user of the booth 80 is able to use the booth 80 in a state immediately after the air environment is improved.

Here, in the exemplary embodiment, while the air environment is being improved by the improvement mechanism 500, the booth 80 is kept in a locked state, and the user is deterred from entering the booth 80 while the air environment is being improved.

As another process, the CPU 111 may also determine to improve the air environment with the improvement mechanism 500 even in a reservation period in the case where the user of the booth 80 is not inside the booth 80.

In the process example illustrated in FIG. 10A, during the reservation period indicated by the sign 10P, the user temporarily exits the booth 80, and a situation in which the user is not present occurs. In other words, a situation in which the booth 80 is empty of people occurs.

In this case, the CPU 111 determines to improve the air environment with the improvement mechanism 500.

More specifically, in the case where the output from the human sensor 25 (see FIG. 2) indicates that the user is not present, the CPU 111 determines that the user is not inside the booth 80, and determines to improve the air environment with the improvement mechanism 500.

With this arrangement, the improvement of the air environment by the improvement mechanism 500 is started in the booth 80. More specifically, in this example, ultraviolet light is radiated from one or more light sources among the light source 510, the movable light source 530, and the ceiling light source 540.

Note that the improvement of the air environment performed in the case where the user is not inside the booth 80 may be performed until the user returns to the booth 80. More specifically, the improvement of the air environment may be performed until output indicating that the user is inside the booth 80 is output from the human sensor 25.

Otherwise, the improvement of the air environment performed in the case where the user is not inside the booth 80 may be performed until a predetermined length of time has elapsed since the user exited the booth 80.

Otherwise, the CPU 111 may determine to improve the air environment with the improvement mechanism 500 on the basis of the elapsed time from the reservation end time of the previous reservation, which is the preceding reservation of the booth 80, to the reservation start time of the next reservation, which is the succeeding reservation of the booth 80.

More specifically, on the basis of the above elapsed time, the CPU 111 may determine to improve the air environment with the improvement mechanism 500 in an unused time period, which is a time period between the reservation end time of the previous reservation and the reservation start time of the next reservation.

More specifically, the CPU 111 determines that a specific process is to be performed by the improvement mechanism 500 in the case where the above elapsed time exceeds a predetermined elapsed time, for example.

In other words, in the case where the above elapsed time exceeds the predetermined elapsed time, the CPU 111 determines to increase the types of processes to be performed by the improvement mechanism 500 compared to the case where the above elapsed time does not exceed the predetermined elapsed time.

Figure 12:
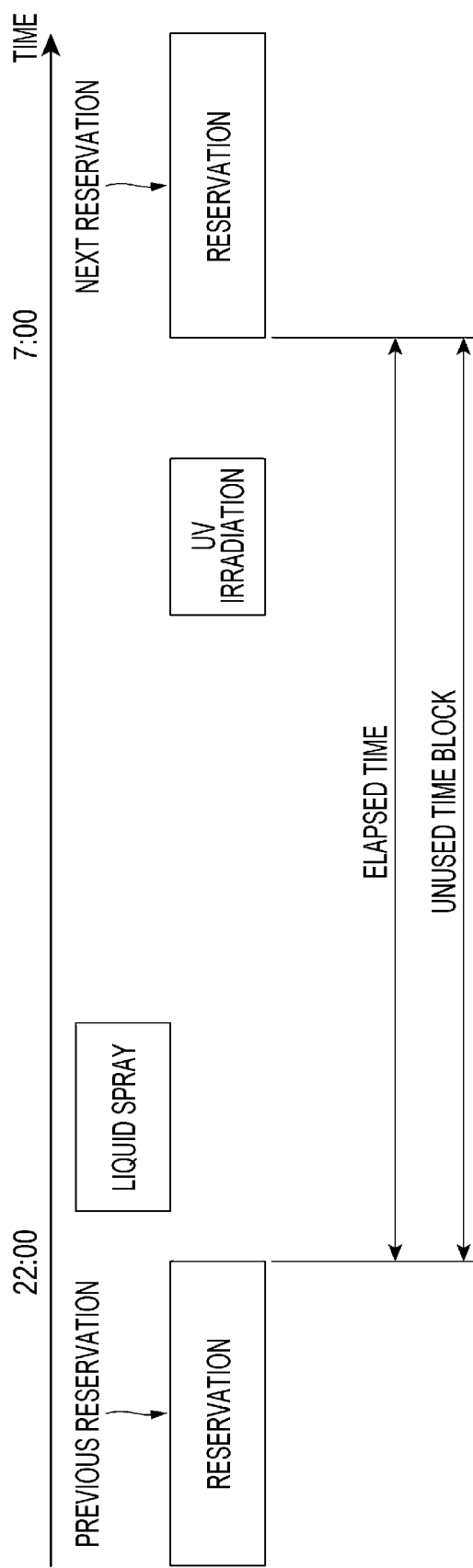
FIG. 12 is a diagram illustrating a process example in a case where an elapsed time exceeds a predetermined elapsed time.

FIG. 12 is a diagram illustrating a process example in a case where the elapsed time exceeds the predetermined elapsed time.

In the case where the elapsed time exceeds the predetermined elapsed time (for example, two hours), the CPU 111 according to the exemplary embodiment determines that not only the radiation of ultraviolet light but also the spraying by the spraying device 520 are to be performed.

In other words, in the case where the elapsed time exceeds the predetermined elapsed time, the CPU 111 determines not only to turn on one or more light sources such as the light source 510, the movable light source 530, and the ceiling light source 540, but also to perform the spraying by the spraying device 520 as an example of the specific process.

In other words, in the case where the elapsed time exceeds the predetermined elapsed time, the CPU 111 determines that not only the radiation of ultraviolet light but also the spraying by the spraying device 520 are to be performed, and thereby determines to increase the types of processes to be performed by the improvement mechanism 500 compared to the case where the above elapsed time does not exceed the predetermined elapsed time.

Here, in the case where one of the processes performed by the improvement mechanism 500 is time-consuming and the above elapsed time is short, it may be difficult to perform the process.

Specifically, in the case where the spraying by the spraying device 520 is time-consuming compared to the radiation of ultraviolet light and the above elapsed time is short, it may be difficult to perform the spraying by the spraying device 520.

In contrast, if the determination to improve the air environment is made with consideration for the elapsed time like in the exemplary embodiment, the spraying by the spraying device 520 may also be performed, and more types of processes may be performed.

Also, as another process, on the basis of the above elapsed time, the CPU 111 may determine a radiation time when performing the radiation of ultraviolet light in the above unused time period (the time period between the reservation end time of the previous reservation and the reservation start time of the next reservation).

More specifically, in this case, if the elapsed time is longer than a predetermined threshold, the CPU 111 lengthens the radiation time of the ultraviolet light, whereas if the elapsed time is shorter than the threshold, the CPU 111 shortens the radiation time of the ultraviolet light compared to the case where the elapsed time is longer than the threshold. With this arrangement, the longer the elapsed time, the ultraviolet light is radiated for a longer length of time.

Note that in the case where the radiation time changes in this way, it is preferable to determine which light sources to turn on, on the basis of the radiation time. Specifically, in this case, if the radiation time of the ultraviolet light is longer than the predetermined threshold as described above for example, it is preferable to turn on only the ceiling light source 540, for example. As another example, in the case where the radiation time of the ultraviolet light is shorter than the above predetermined threshold, it is preferable to turn on only the light source 510 or to turn on both the light source 510 and the ceiling light source 540.

Also, as another process, the CPU 111 may also make a determination regarding the frequency of the improvement of the air environment to be performed by the improvement mechanism 500 on the basis of the acquired reservation information, for example.

Specifically, in the case of performing this process, the CPU 111 ascertains the number of reservations per unit time and the total reserved time per unit time on the basis of the acquired reservation information, for example.

Here, the total reserved time refers to the length of time obtained by totaling the reservation times of each of the reservations that have been made within a unit time.

More specifically, for example, every time a predetermined time is reached, the CPU 111 ascertains the number of reservations and the total reserved time from the predetermined time to the time when a predetermined length of time elapses.

Additionally, on the basis of the number of reservations and the total reserved time, the CPU 111 determines the frequency of the improvement of the air environment to be performed by the improvement mechanism 500 from the above predetermined time to the time when the predetermined length of time elapses, for example.

Specifically, for example, in the case where the number of reservations or the total reserved time exceeds a predetermined threshold, the CPU 111 determines to increase the number of times the air environment is to be improved by the improvement mechanism 500 from the above predetermined time to the time when the predetermined length of time elapses compared to the case where the number of reservations or the total reserved time does not exceed the predetermined threshold.

In the case of performing this process, the more frequently the booth 80 is used, the air environment is improved more often.

Note that in this case, like the case described earlier, it is likewise preferable for the improvement of the air environment by the improvement mechanism 500 to be performed basically in a time period in which the booth 80 is not reserved.

Also, as another example, the CPU 111 may make a determination regarding the degree of the improvement of the air environment by the improvement mechanism 500 on the basis of the acquired reservation information.

Specifically, in this case, the CPU 111 ascertains the number of reservations per unit time and the total reserved time per unit time on the basis of the acquired reservation information similarly to the example described above, for example.

More specifically, for example, every time a predetermined time is reached, the CPU 111 ascertains the number of reservations and the total reserved time from the predetermined time to the time when a predetermined length of time elapses.

Additionally, on the basis of the number of reservations and the total reserved time, the CPU 111 determines the degree of the improvement of the air environment to be performed by the improvement mechanism 500 from the above predetermined time to the time when the predetermined length of time elapses.

Specifically, for example, in the case where the number of reservations or the total reserved time exceeds a predetermined threshold, the CPU 111 determines to extend the duration of the improvement of the air environment by the improvement mechanism 500 from the above predetermined time to the time when the predetermined length of time elapses compared to the case where the number of reservations or the total reserved time does not exceed the predetermined threshold.

More specifically, the CPU 111 determines to extend the duration of each cycle of the improvement of the air environment performed by the improvement mechanism 500.

Also, as another example, in the case where the number of reservations or the total reserved time exceeds a predetermined threshold, the CPU 111 determines to increase the output of the improvement mechanism 500 from the above predetermined time to the time when the predetermined length of time elapses compared to the case where the number of reservations or the total reserved time does not exceed the predetermined threshold.

If the output of the improvement mechanism 500 is increased, the amount sprayed when the spraying device 520 sprays the liquid is increased, and the amount of ultraviolet light emitted by the light source 510, the movable light source 530, and the ceiling light source 540 is increased.

Also, as described above, the exemplary embodiment is configured such that the spot irradiated with light may be changed.

More specifically, in the exemplary embodiment, the attitude of the movable light source 530 may be changed as described above, and the spot irradiated with light may be changed.

The CPU 111 may also make a determination regarding the spot to be irradiated with light emitted from the movable light source 530 on the basis of the acquired reservation information.

Specifically, in the case where the acquired reservation information satisfies a specific condition, the CPU 111 determines to irradiate a specific spot inside the booth 80 with ultraviolet light.

Specifically, the CPU 111 ascertains the number of reservations and the total reserved time per unit time similarly to the above, for example. Additionally, in the case where number of reservations or the total reserved time exceeds a predetermined threshold, the CPU 111 determines to irradiate the baggage container 93 (see FIG. 3) with ultraviolet light, for example.

The baggage container 93 is not contaminated as easily as objects such as the desk 92 (see FIG. 3), and therefore the frequency of irradiation with ultraviolet light may be lowered compared to the desk 92 and the like. On the other hand, in cases where the booth 80 is being used frequently, it is anticipated that the baggage container 93 will become contaminated.

Accordingly, in the exemplary embodiment, in the case where number of reservations or the total reserved time exceeds a predetermined threshold as above, the CPU 111 determines to irradiate the baggage container 93 with ultraviolet light.

With this arrangement, in the exemplary embodiment, the movable light source 530 is pointed toward the baggage container 93, and the baggage container 93 is irradiated with ultraviolet light.

Note that although the above describes a case where the air environment inside the booth 80 is improved by the improvement mechanism 500, the improvement of the air environment inside the booth 80 may also be performed by cleaning personnel in addition to the improvement mechanism 500 in some cases.

More specifically, for example, the specific process such as the spraying of liquid described above may also be performed by cleaning personnel in some cases.

In the case where the improvement of the air environment is performed by cleaning personnel, the CPU 111 preferably makes a determination regarding the improvement of the air environment to be performed by the improvement mechanism 500 with additional consideration for the work schedule of the cleaning personnel.

In other words, the CPU 111 preferably makes a determination regarding the improvement of the air environment to be performed by the improvement mechanism 500 on the basis of the reservation information and also schedule information, which is information about the work schedule of the cleaning personnel.

Here, in the case where the spraying of liquid is performed by cleaning personnel as described above, for example, the CPU 111 ascertains the timing for the spraying of liquid by the cleaning personnel from the schedule information.

Additionally, on the basis of the timing and the reservation information, the CPU 111 determines the timing at which to radiate ultraviolet light using the movable light source 530, the light source 510, or the ceiling light source 540.

More specifically, in this case, the CPU 111 determines to radiate ultraviolet light after the spraying of liquid by the cleaning personnel and also in a time period in which the booth 80 is not reserved by a user.

More preferably, in this case, the CPU 111 determines to radiate ultraviolet light after the spraying of liquid by the cleaning personnel and also before the reservation time period of the first reservation after the spraying.

Also, typical processes such as sweeping, wiping down surfaces, and taking out trash may also be performed by cleaning personnel in some cases. In such a case, the CPU 111 likewise makes a determination regarding the improvement of the air environment by the improvement mechanism 500, such as the timing of the spraying of the liquid and the timing of the radiation of ultraviolet light, with consideration for the work schedule information of the cleaning personnel.

Specifically, in this case, the CPU 111 determines to improve the air environment with the improvement mechanism 500 when the air environment is not improved by the cleaning personnel and also in a time period in which the booth 80 is not reserved by a user.

Another Exemplary Configuration

Figure 13:
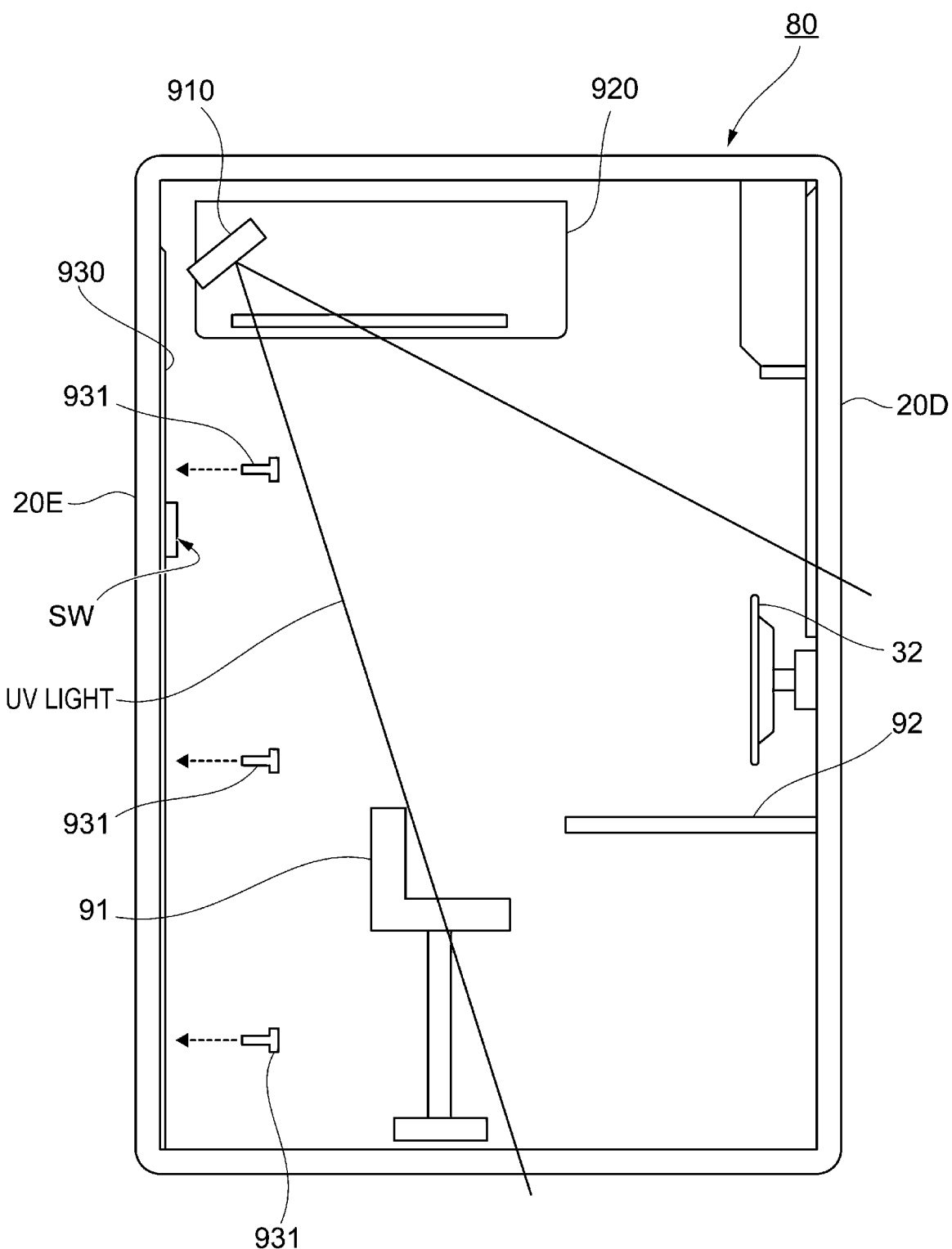
FIG. 13 is a diagram illustrating another exemplary configuration of the booth.

FIG. 13 is a diagram illustrating another exemplary configuration of the booth 80. In FIG. 13, the wall 20C (see FIG. 2) and the door 22 are omitted from illustration.

Like the configuration described above, this exemplary configuration is provided with a light source 910 that emits ultraviolet light containing ultraviolet rays.

The light source 910 is provided on the opposite side from the side where the monitor 32 and the desk 92 are provided, and emits ultraviolet light toward the monitor 32 and the desk 92 from the opposite side. In other words, the light source 910 emits ultraviolet light diagonally downward, thereby irradiating the monitor 32 and the desk 92 positioned below the light source 910 with ultraviolet light.

The booth 80 is provided with two walls 20D and 20E disposed parallel to each other, but in this exemplary configuration, the monitor 32 and the desk 92 are installed on the side where one of the two walls 20D and 20E are provided, and the light source 910 is installed on the side where the other wall is provided.

Additionally, in the present exemplary embodiment, an air conditioner 920 that discharges hot or cold air is provided farther back than the light source 910.

Furthermore, in the present exemplary embodiment, an interior finishing member 930 that is a member for decorating the interior of the booth 80 is provided inside the booth 80 on the side where the wall 20E is provided. In other words, the interior finishing member 930 that is a member for finishing the interior of the booth 80 is provided. The interior finishing member 930 is secured to an inner surface of the booth 80 by multiple screws 931.

Specifically, multiple screw holes (not illustrated) are provided in an inner surface of the booth 80, and the interior finishing member 930 is caught between the portions where the screw holes are provided and the heads of the screws 931, thereby securing the interior finishing member 930.

Note that, although omitted from illustration, the interior finishing member 930 is also provided in portions other than the portion where the wall 20E is provided among the inner surfaces of the booth 80.

Furthermore, a lock/unlock switch SW operated by the user when the user locks or unlocks the door 22 (see FIG. 2) is provided in the portion positioned on an inner surface of the booth 80 on the wall 20E side.

In the present exemplary embodiment, when the user operates the lock/unlock switch SW, the electronic lock 22C (see FIG. 2) is activated and the booth 80 is locked or unlocked.

Figure 14:
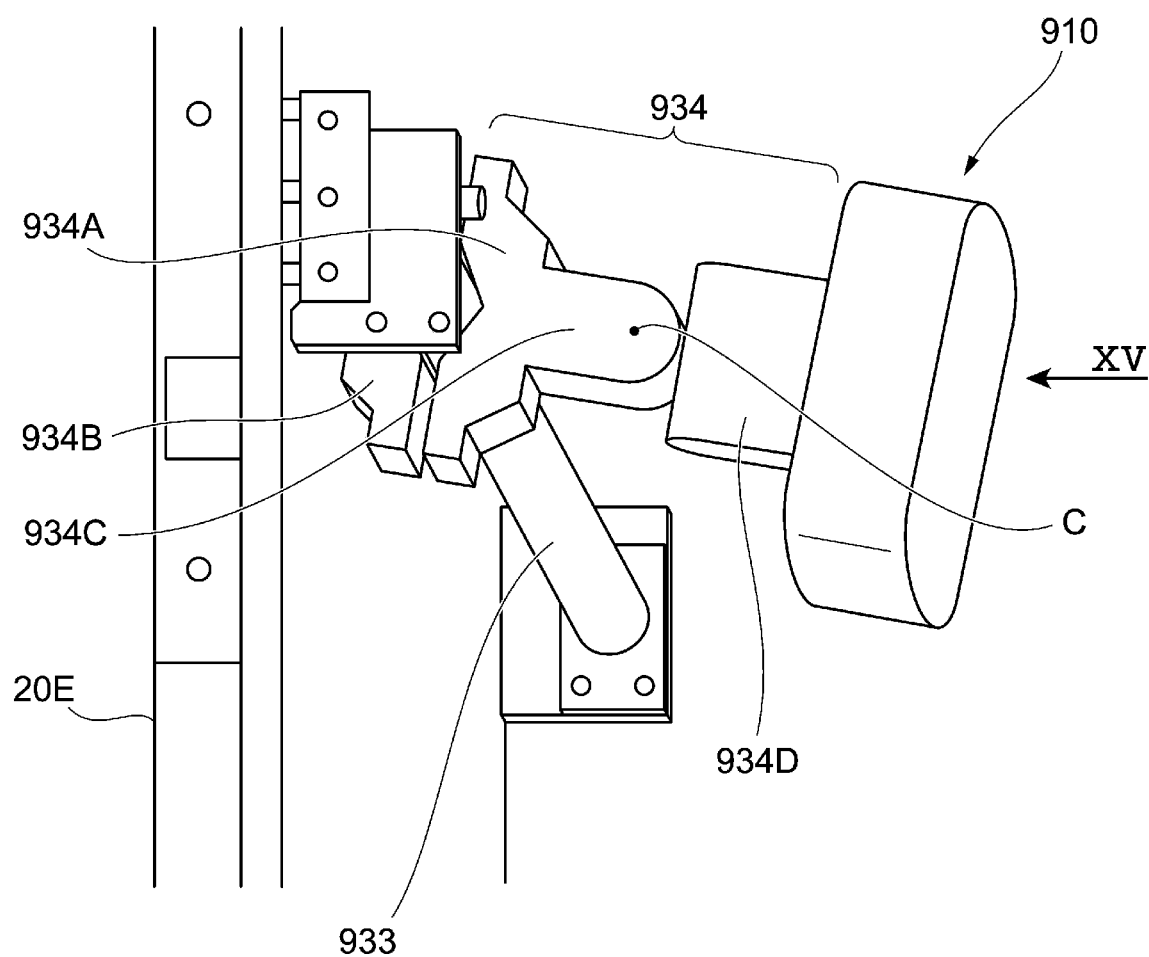
FIG. 14 is an enlarged perspective view of a portion of the light source illustrated in FIG. 13.

FIG. 14 is an enlarged perspective view of a portion of the light source 910 illustrated in FIG. 13.

In this exemplary configuration, a cylindrical support member 933 extending from the front toward the back of the booth 80 is provided.

In other words, in this exemplary configuration, the support member 933 extending along the wall 20E is provided. In this exemplary configuration, the light source 910 is supported by the support member 933.

A connecting member 934 that connects the light source 910 and the support member 933 is provided between the light source 910 and the support member 933, and the light source 910 is secured to the support member 933 through the connecting member 934.

The connecting member 934 is provided with a first member 934A disposed closer to the light source 910 than the support member 933, and a second member 934B disposed closer to the wall 20E than the support member 933. In this exemplary configuration, the support member 933 is caught by the first member 934A and the second member 934B, thereby securing the connecting member 934 to the support member 933.

Additionally, the exemplary configuration is provided with a securing part 934C that is secured to the support member 933, and a rotating part 934D which is rotatably provided with respect to the securing part 934 and which is configured to rotate about a center of rotation C.

In this exemplary configuration, the light source 910 is attached to the rotating part 934D, such that when the rotating part 934D rotates, the direction of the light source 910 is changed.

FIG. 15 is a diagram of a case of viewing the support member 933 and the light source 910 from the direction indicated by the arrow XV in FIG. 14.

The support member 933 is disposed extending horizontally in the diagram. In this exemplary embodiment, the light source 910 is allowed to move in the extension direction of the support member 933.

Also, FIG. 15 illustrates a state in which the light source 910 is placed near the entrance to the booth 80.

From this state, if the light source 910 is moved in the direction indicated by the arrow 15A and positioned at the location indicated by the dashed lines 15B, the light source 910 is positioned near the back of the booth 80.

In this state with the light source 910 positioned near the back of the booth 80, the user is able to enter and exit the booth 80 easily.

On the other hand, in the state with the light source 910 positioned near the entrance to the booth 80, the light source 910 is placed near the door 22 (see FIG. 2), and the door 22 that is frequently touched by the user is easily irradiated with ultraviolet light.

Also, in the state with the light source 910 placed near the entrance of the booth 80, damage or malfunction of the lock/unlock switch SW (see FIG. 13) installed near the entrance does not occur easily.

The exemplary configuration is provided with a rod-shaped support member 933, and anticipates that an object of the user's belongings, such as an umbrella, may be hung on the support member 933.

In this case, if an object of the user's belongings is hung in the portion of the support member 933 positioned above the lock/unlock switch SW, there is a risk that the hanging object may contact the lock/unlock switch SW.

Also, in the case where the object is an umbrella, there is a risk that water droplets may adhere to the lock/unlock switch SW.

In contrast, the in state with the light source 910 placed near the entrance to the booth 80, the light source 910 is positioned above the lock/unlock switch SW.

In this case, an object of the user's belongings is not hung in the portion of the support member 933 positioned above the lock/unlock switch SW, and damage or malfunction of the lock/unlock switch SW caused by such an object does not occur easily.

Note that although the light source 910 is moved manually in the present exemplary embodiment, the configuration is not limited thereto, and a driving mechanism for moving the light source 910 may also be provided.

Additionally, the driving mechanism may be activated according to an instruction from the user or according to an instruction from a control device provided in the booth 80 or the CPU 111 of the space management server 5 (see FIG. 5), and the light source 910 may be moved automatically.

This exemplary configuration describes a case where the support member 933 includes a cylindrical member as an example. However, the shape of the support member 933 is not limited thereto, and the support member 933 may also include a member having another shape, such as a square pillar member.

Otherwise, a grooved rail may also be provided along the wall 20E, and the light source 910 may be configured to move along the grooved rail.

Also, another exemplary configuration is possible in which the light source 910 is configured to move such that the light source 910 moves closer to the monitor 32 and the desk 92, and also such that the light source 910 moves away from the monitor 32 and the desk 92.

In other words, light source 910 may also be configured to move such that the light source 910 moves closer to the irradiation target to be irradiated with ultraviolet light from the light source 910, and also such that the light source 910 moves away from the irradiation target.

In this case, the ultraviolet light irradiating an irradiation target such as the monitor 32 or the desk 92 is increased in intensity.

More specifically, the monitor 32 and the desk 92 are used frequently by the user, and are easily contaminated with substances such as filth and viruses. If the light source 910 is configured to move, the ultraviolet light irradiating locations that are easily contaminated with substances such as filth and viruses is increased in intensity.

Figure 16A:
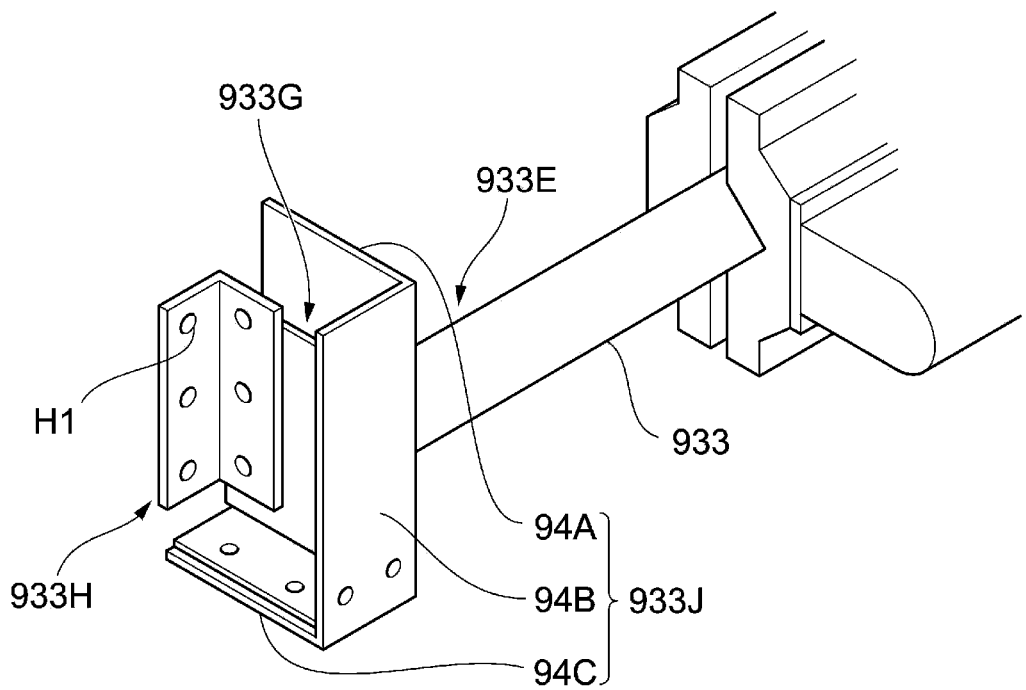
FIGS. 16A and 16B are diagrams explaining a first end and a second end of the support member.
Figure 16B:
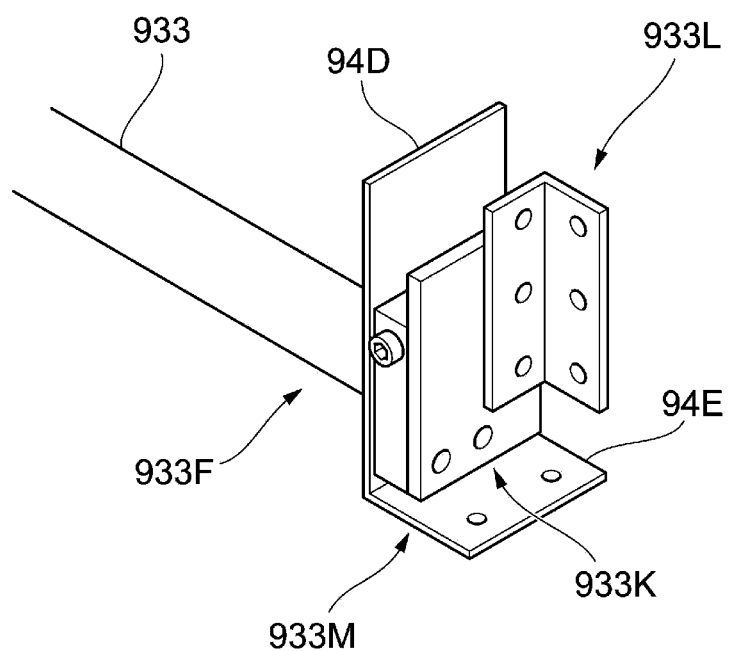

FIGS. 16A and 16B are diagrams explaining a first end 933E and a second end 933F of the support member 933.

Specifically, FIG. 16A is a diagram of a case of viewing the first end 933E of the support member 933 from the direction of the arrow XVIA in FIG. 15. FIG. 16B is a diagram of a case of viewing the second end 933F of the support member 933 from the direction of the arrow XVIB in FIG. 15.

As illustrated in FIG. 16A, the first end 933E of the support member 933 is provided with a tabular securing member 933G secured to the first end 933E, a secured member 933H having an L-shaped cross-section to which the securing member 933G is secured, and a covering member 933J that covers the securing member 933G and the secured member 933H.

The covering member 933J includes a second end covering part 94A that faces the second end 933F of the support member 933 (see FIG. 15), a desk-side covering part 94B that faces the desk 92 (see FIG. 13), and a bottom covering part 94C that faces down.

In the present exemplary embodiment, by installing the covering member 933J, the securing member 933G and the secured member 933H are not visible to the user, thereby avoiding a depreciation in the appearance of the interior finishing of the booth 80.

In the present exemplary embodiment, by securing the secured member 933H to an inner surface of the booth 80, the first end 933E of the support member 933 is secured to the booth 80.

More specifically, in the present exemplary embodiment, the screws 931 for securing the interior finishing member 930 (see FIG. 13) are used to secure the support member 933 that supports the light source 910 to the booth 80.

Specifically, the secured member 933H is installed in addition to interior finishing member 930 between the head of one of the multiple screws 931 and one of the screw holes. Thereafter, the screws 931 are used to secure the secured member 933H as well.

More specifically, one of the screws 931 is made to pass through a penetrating hole H1 provided in the secured member 933H (see FIG. 16A) to secure the secured member 933H together with the interior finishing member 930.

The configuration on the second end 933F side of the support member 933 will be described.

As illustrated in FIG. 16B, the second end 933F of the support member 933 likewise is provided with a securing member 933K secured to the second end 933F of the support member 933, a secured member 933L having an L-shaped cross-section to which the securing member 933K is secured, and a covering member 933M that covers the securing member 933K and the secured member 933L.

In this exemplary configuration, by securing the secured member 933L to an inner surface of the booth 80, the second end 933F of the support member 933 is secured to the inner surface.

The covering member 933M includes a first end covering part 94D that faces the first end 933E of the support member 933 (see FIG. 15), and a bottom covering part 94E that faces down.

In the present exemplary embodiment, by installing the covering member 933M, the securing member 933K and the secured member 933L are not visible to the user, thereby avoiding a depreciation in the appearance of the interior finishing of the booth 80.

Note that, as described above, the desk-side covering part 94B that faces the desk 92 is provided in the covering member 933J (see FIG. 16A) provided on the first end 933E side of the support member 933, but a portion corresponding to the desk-side covering part 94B may also be provided in the covering member 933M (see FIG. 16B) provided on the second end 933F side of the support member 933.

In this exemplary configuration, the air conditioner 920 is provided in a location positioned closer to the desk 92 than the securing member 933K (see FIG. 16B) and the secured member 933L, as illustrated in FIG. 13.

In this exemplary configuration, by providing the air conditioner 920, the securing member 933K and the secured member 933L are not visible from the desk 92. Consequently, in this exemplary configuration, the installation of the portion corresponding to the desk-side covering part 94B is omitted.

Note that like the first end 933E, in the second end 933F, the screw holes and screws 931 for securing the interior finishing member 930 are also used to secure the secured member 933L (see FIG. 16B).

Figure 17:
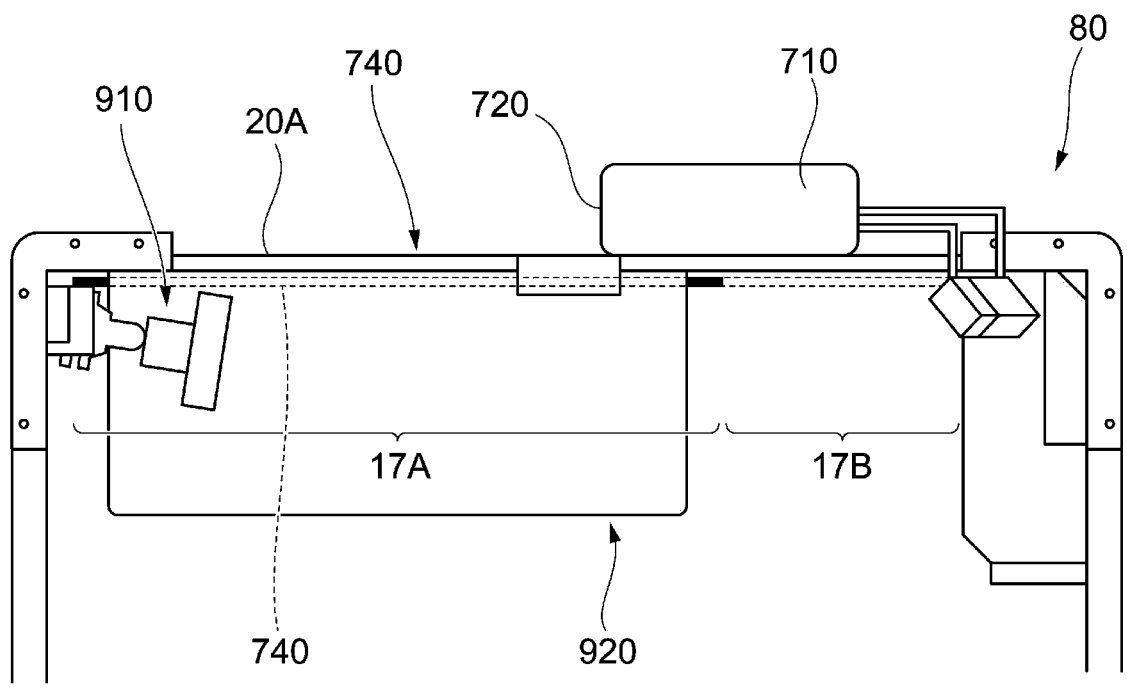
FIG. 17 is a diagram illustrating a configuration of an upper part of the booth.

FIG. 17 is a diagram illustrating a configuration of the upper part of the booth 80.

In this exemplary configuration, a timer power supply 710 that provides or stops a supply of power at predetermined times is provided above the ceiling 20A of the booth 80.

The timer power supply 710 is housed in a housing container 720 that keeps dust and the like from adhering to the timer power supply 710.

Additionally, a cable 740 that connects the light source 910 and the timer power supply 710 is provided.

The cable 740 is disposed inside the booth 80 in the region indicated by the sign 17A, and is disposed outside the booth 80 in the region indicated by the sign 17B.

In other words, the cable 740 passes outside the booth 80 on the way to the timer power supply 710.

The timer power supply 710 controls the switching on and off of the power supply according to the time. With this arrangement, in the present exemplary embodiment, the light source 910 is turned on when a predetermined time is reached, and the light source 910 is also turned off when a predetermined time is reached.

Note that the control of the light source 910 is not limited to the above, and may also be performed by the CPU 111 provided in the space management server 5 or by a control device (not illustrated) provided in the booth 80.

Figure 18B:
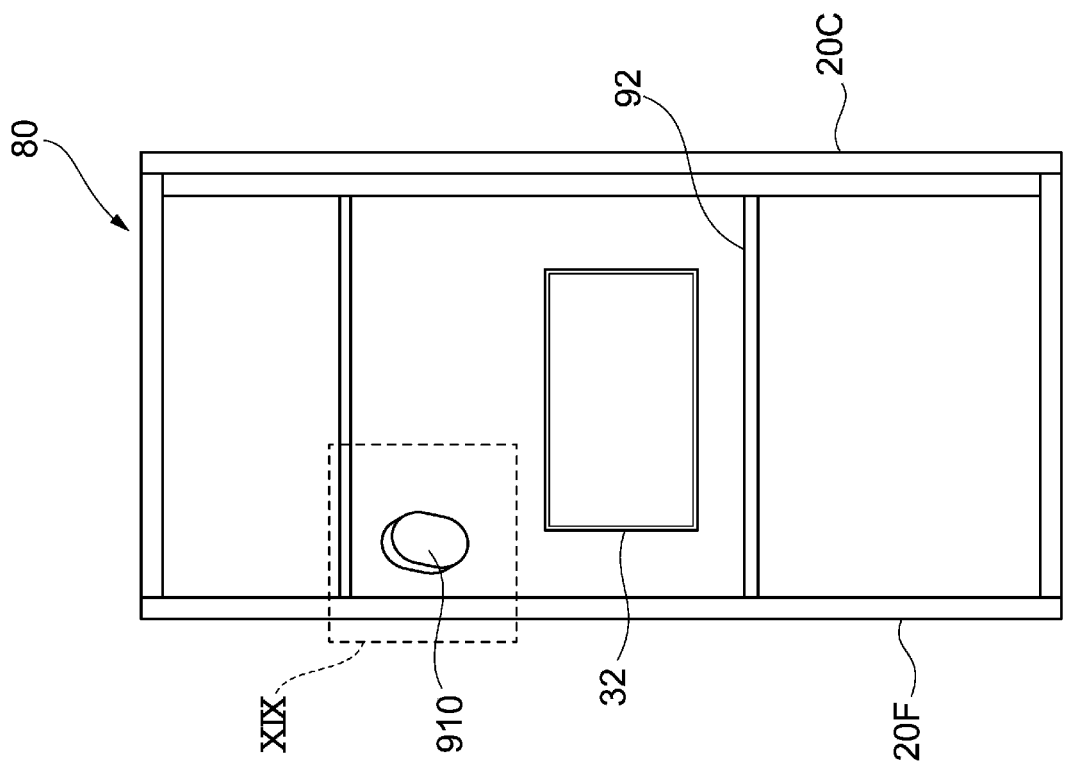
FIGS. 18A and 18B are diagrams illustrating another configuration of the booth.
Figure 18A:
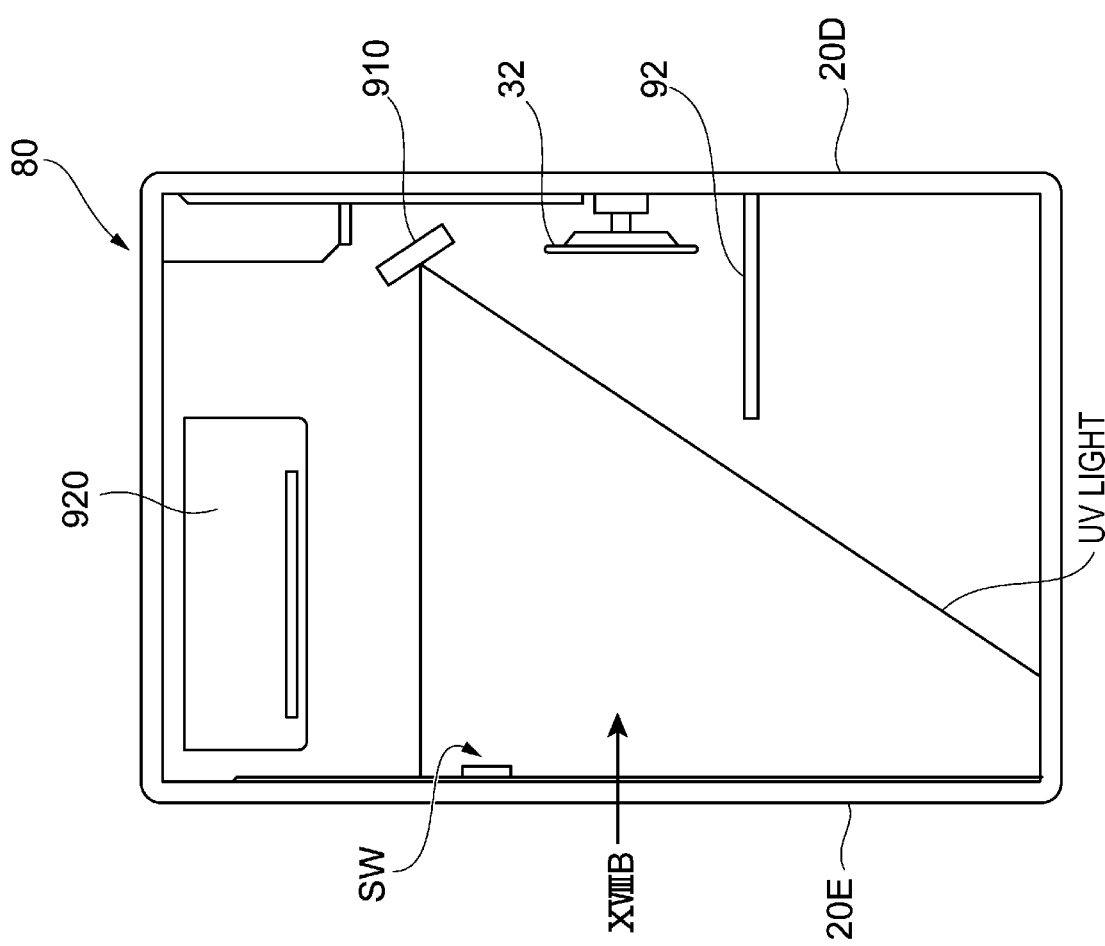

FIGS. 18A and 18B are diagrams illustrating another configuration of the booth 80. FIG. 18A is a front view of the booth 80, while FIG. 18B is a diagram of a case of viewing the interior of the booth 80 from the direction indicated by the arrow XVIIIB in FIG. 18A.

In this exemplary configuration, the light source 910 is provided on the side of the wall 20D from among the two walls 20D and 20E disposed parallel to each other.

In other words, in this exemplary configuration, the light source 910 is installed on the same side as the side where the monitor 32 and the desk 92 are provided.

Additionally, in this exemplary configuration, ultraviolet light is emitted from the light source 910 toward the side where the wall 20E is provided.

In this exemplary configuration, the door 22 (see FIG. 2) is irradiated with more ultraviolet light compared to the exemplary configuration illustrated in FIG. 13. Particularly, the portion of the handle provided on the inner side of the door 22 is irradiated with more ultraviolet light. In other words, the portion of the door 22 that the user touches frequently is irradiated with more ultraviolet light.

Also, in this exemplary configuration, the lock/unlock switch SW that the user touches frequently is irradiated with more ultraviolet light compared to the exemplary configuration illustrated in FIG. 13.

Also, in this exemplary configuration, as illustrated in FIG. 18B, the light source 910 is disposed close to the wall 20F positioned in the back. However, the configuration is not limited to the above, and the light source 910 may also be disposed close to the wall 20C positioned on the side where the door 22 (see FIG. 2) is provided.

In addition, multiple light sources 910 may also be installed, and the multiple light sources 910 may installed both on the opposite side from the monitor 32 (see FIG. 13) and on the side near the monitor 32 (see FIG. 18A), for example.

Figure 19:
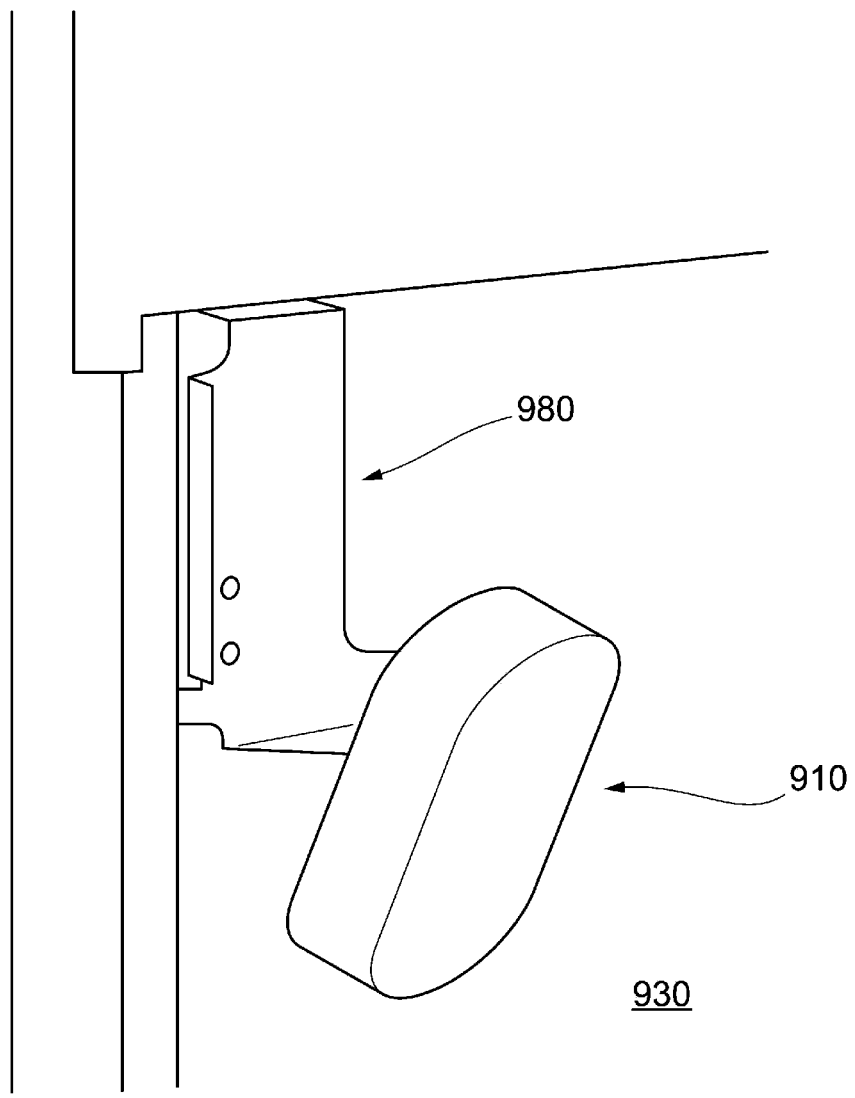
FIG. 19 is an enlarged view of the portion indicated by the sign XIX in FIG. 18B.

FIG. 19 is an enlarged view of the portion indicated by the sign XIX in FIG. 18B.

In this exemplary configuration, a support member 980 that supports the light source 910 is provided. In this exemplary configuration, the back side of the light source 910 is supported by the support member 980. Furthermore, in this exemplary configuration, the support member 980 is hook-shaped, and the support member 980 is hung on the upper edge of the interior finishing member 930.

Figure 20B:
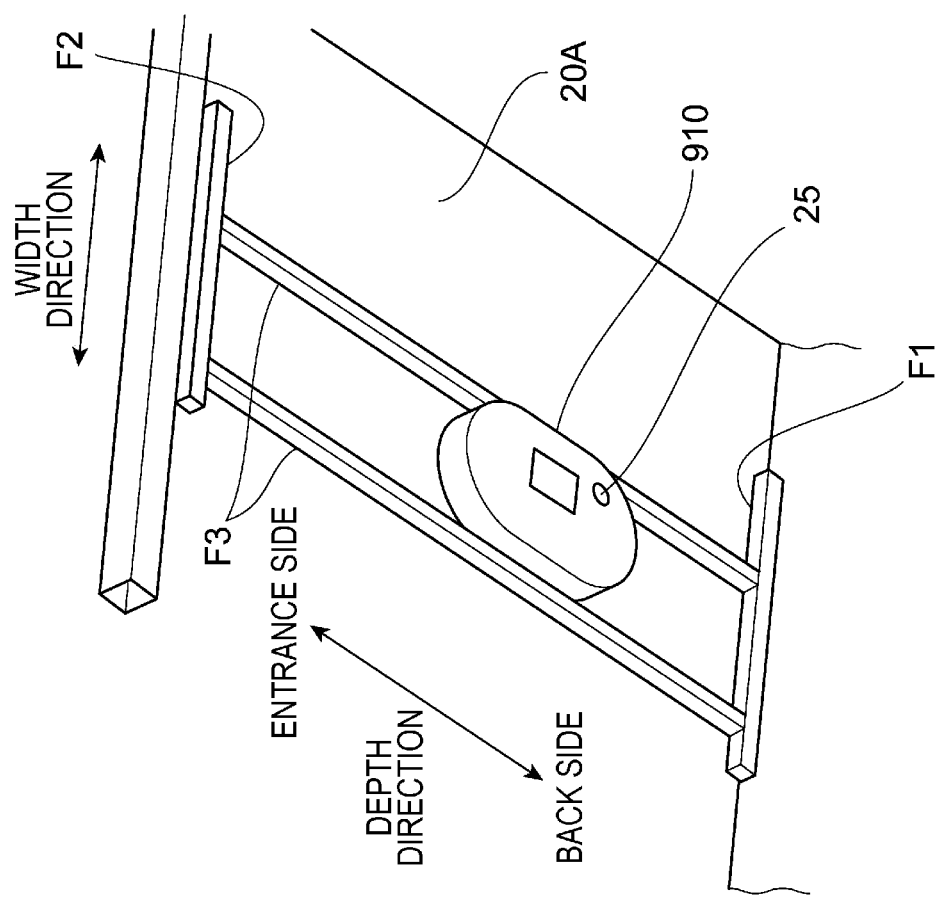
FIGS. 20A and 20B are diagrams illustrating another exemplary configuration of the booth.
Figure 20A:
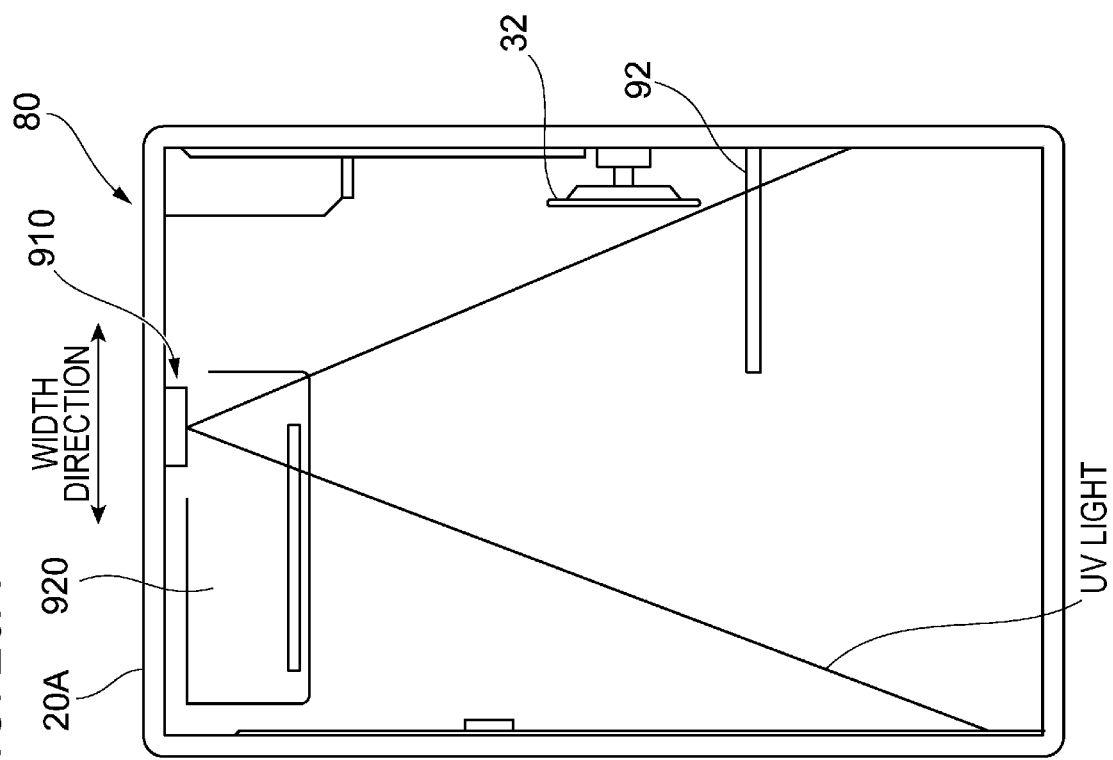

FIGS. 20A and 20B are diagrams illustrating another exemplary configuration of the booth 80.

FIG. 20A is a front view of the booth 80. FIG. 20B is a perspective view in the case of viewing the ceiling 20A of the booth 80 obliquely from below.

In this exemplary configuration, as illustrated in FIGS. 20A and 20B, the light source 910 is installed on the ceiling 20A of the booth 80, and ultraviolet light is emitted downward from the light source 910. In other words, ultraviolet light irradiates the booth 80 from top to bottom.

Specifically, as illustrated in FIG. 20B, the light source 910 is disposed generally in a central part in the depth direction of the booth 80. Also, as illustrated in FIG. 20A, the light source 910 is disposed in a central part in the width direction of the booth 80.

In this exemplary configuration, ultraviolet light easily irradiates the entire interior of the booth 80, without being biased toward a certain spot to be irradiated with ultraviolet light.

As illustrated in FIG. 20B, in this exemplary configuration, a back-side frame F1 secured to the booth 80 and extending in the width direction of the booth 80 is provided near the back of the booth 80, and a front-side frame F2 similarly secured to the booth 80 and extending in the width direction is provided near the entrance to the booth 80.

Additionally, in this exemplary configuration, two support frames F3 extending in the depth direction of the booth 80 and supported by the back-side frame F1 and the front-side frame F2 are provided.

In this exemplary configuration, the light source 910 is installed between the two support frames F3, and the light source 910 is also supported by the two support frames F3.

Also, in this exemplary configuration, the light source 910 is provided with a human sensor 25.

Lighting Control of Light Source

Lighting control of the light source 510, the movable light source 530, the ceiling light source 540, and the light source 910 illustrated in FIGS. 2 to 4 and FIGS. 13 to 20A and 20B will be described. In the following description, these light sources are simply referred to as the "light source 970" without being distinguished individually.

(1) One conceivable mode of turning on the light source 970 is to turn on the light source 970 outside a reservation period of the booth 80, for example. In other words, a mode that turns on the light source 970 during a time period in which a user is unable to reserve the booth 80 is conceivable as an example.

Specifically, for example, a mode that turns on the light source 970 at 5:00 AM in the morning or in the middle of the night is conceivable.

(2) Another conceivable mode of turning on the light source 970 is to turn on the light source 970 on the basis of a detection result from the human sensor 25, for example. More specifically, a mode that turns on the light source 970 in the case where the detection result from the human sensor 25 indicates that a person is not present is conceivable.

In this case of this mode, irradiation with ultraviolet light is performed at timings when the booth 80 is unoccupied, irrespectively of whether or not the booth 80 has been reserved. In this mode, the booth 80 is irradiated with ultraviolet light for a longer time in cases where the utilization rate of the booth 80 is low, and the interior of the booth 80 is sterilized to a higher degree.

(3) Another conceivable mode of turning on the light source 970 is to secure dedicated times for sterilization during the operating hours of the booth 80 (that is, the time period during which the booth 80 is reservable), and turn on the light source 970 during the dedicated times.

In other words, a mode is conceivable in which times when the booth 80 is unavailable for reservation are secured between the operating start time and the operating end time of the booth 80, and the light source 970 is turned on during the times when the booth 80 is unavailable for reservation.

Specifically, for example, 30 minutes for turning on the light source 970 are secured at 10:00 AM and 16:00 PM. Note that in this case, the booth 80 preferably is locked to keep a user from entering the booth 80.

In this mode, mandatory times for irradiation with ultraviolet light are secured, and situations in which the booth 80 is not sufficiently irradiated with ultraviolet light do not occur as easily.

(4) Also, another conceivable mode of turning on the light source 970 is to turn on the light source 970 between a reservation period and a subsequent reservation period of the booth 80, for example. In other words, a mode that turns on the light source 970 during a time period between a first reservation time period and a subsequent reservation time period for the booth 80 is conceivable. Here, a conceivable mode of reserving the booth 80 is to disallow consecutive reservations (that is, make reservations by respectively different users non-consecutive), and secure an empty time with no reservation between a reservation by a first user and the next reservation by another user different from the first user.

In this case, the light source 970 is turned on during the empty time between the reservation by the first user and the reservation by the other user.

More specifically, for example, 15 minutes are secured as the empty time with no reservation between the reservation by the first user and the reservation by the other user, and the booth 80 is irradiated with ultraviolet light during the 15 minutes.

(5) Besides the above, the target of irradiation with ultraviolet light may not be fixed to a single spot, and specific spots inside the booth 80 may be irradiated with ultraviolet light in a concentrated way by changing the direction and position of the light source 970, for example.

In other words, by making it possible to change the irradiation position of the light emitted from the light source 970, specific spots inside the booth 80 may be irradiated with ultraviolet light in a concentrated way.

Specifically, for example, the interior of the booth 80 is irradiated with ultraviolet light over a wide range normally, but immediately after the booth 80 has been used by a user, spots that the user has touched or spots where airborne droplets produced by the user coughing have possibly adhered are irradiated with ultraviolet light in a concentrated way.

In other words, the irradiation position of light emitted from the light source 970 is changed such that spots inside the booth 80 that the user has touched and/or spots inside the booth 80 where saliva (airborne droplets) from the user's mouth has adhered are irradiated with ultraviolet light.

More specifically, in the case of performing the above process, an image acquired by the interior imaging device 24 (see FIG. 2) installed in the booth 80 is analyzed to ascertain spots that the user has touched and spots where saliva may have adhered.

Thereafter, a driving mechanism that moves the light source 970 or changes the direction of the light source 970 is controlled such that the spots that the user has touched and the spots where saliva may have adhered are irradiated with ultraviolet light in a concentrated way.

Otherwise, the light source 970 may be configured to be movable, and when irradiating an irradiation target with ultraviolet light, the light source 970 may be brought close to the irradiation target.

In this case, the light source 970 may be installed in a location that does not obstruct the user when the user uses the booth 80 normally. Also, when irradiating an irradiation target with ultraviolet light, the light source 970 may be placed close to the irradiation target to sterilize the irradiation target more effectively.

In addition, the output of the light source 970 and the duration of the irradiation with ultraviolet light may also be changed according to the distance between the irradiation target to be irradiated with ultraviolet light and the light source 970.

Specifically, for example, in the case where the distance between the irradiation target and the light source 970 is greater than a predetermined threshold, the output of the light source 970 may be increased and the duration of the irradiation with ultraviolet light may be lengthened to ensure that the irradiation target is irradiated with ultraviolet light with sufficient intensity.

On the other hand, in the case where the distance between the irradiation target and the light source 970 is less than a predetermined threshold, the output of the light source 970 may be decreased and the duration of the irradiation with ultraviolet light may be shortened.

(6) Also, the output of ultraviolet light does not have to be constant and may also be varied.

Specifically, for example, when irradiating spots that the user has touched and spots where saliva may have adhered, the output of ultraviolet light may be increased to irradiate the spots with more intense ultraviolet light.

To irradiate spots with more intense ultraviolet light, the number of light sources 970 to turn on may be increased such that the irradiation target is irradiated with ultraviolet light from more light sources 970, for example.

As another example, the light source 970 to use may be switched such that ultraviolet light is emitted from a light source 970 that radiates ultraviolet light in a localized way. With this arrangement, spots that the user has touched and spots where saliva may have adhered likewise are irradiated with ultraviolet light in a concentrated way.

(7) Additionally, when irradiating an irradiation target with ultraviolet light from the light source 970, the light source 970 may also be turned on intermittently rather than being kept on continuously. In other words, the light source 970 may be turned on and off repeatedly to irradiate the interior of the frame 81 forming the booth 80 with light.

The light source 970 also products heat, and by turning on the light source 970 intermittently in this way, a temperature rise in the light source 970 may be suppressed.

Note that when turning on the light source 970 intermittently in this way, a total ON duration since a predetermined reference time is ascertained, and the intermittent lighting is continued until the total ON duration reaches a predetermined target value, for example.

With this arrangement, incomplete sterilization of the interior of the booth 80 may be avoided compared to the case of ending the intermittent lighting without setting a target value.

(8) Also, the light source 970 may be activated on the basis of a detection result from any of various types of sensors as described above.

Specifically, for example, the light source 970 may be turned on in the case where a detection result from the human sensor 25 indicates that a person is not present inside the booth 80 as described above.

As another example, the light source 970 may also be turned on in the case where a detection result from the human sensor 25 indicates that a person is not present inside the booth 80 and a detection result from the open/close sensor S1 (see FIG. 2) also indicates that the door 22 is closed.

Furthermore, in addition to the human sensor 25, a proximity sensor that detects whether or not the user is near the light source 970 may also be provided.

The proximity sensor detects the user in the case where the user is within a predetermined distance from the light source 970.

If the proximity sensor is provided in addition to the human sensor 25, a situation where the light source 970 is turned on even though a person is present inside the booth 80 may be avoided.

Here, with a configuration provided with the human sensor 25 only, if the user inside the booth 80 is in a still, motionless state, the user may not be detected, and consequently there are concerns that the light source 970 may be turned on.

The human sensor 25 is a sensor that detects human motion in the booth 80 to detect the presence or absence of the user inside the booth 80. In this case, if the user inside the booth 80 is in a still, motionless state, the user may not be detected, and there are concerns that the light source 970 may be turned on.

In contrast, if the proximity sensor is provided in addition to the human sensor 25, the user may be detected if the user is near the light source 970, even if the user is in a still, motionless state. Furthermore, in this case, the off-state of the light source 970 is maintained.

The proximity sensor may be provided in the light source 970, or the proximity sensor may be configured separately from the light source 970 and provided in a location separate from the installation location of the light source 970.

Note that another method of detecting the presence of a still, motionless user is to use a seat sensor installed in the chair 91, for example.

If the seat sensor is provided in addition to the human sensor 25, the user may be detected if the user is sitting in the chair 91, even if the user is in a still, motionless state. Furthermore, in this case, the off-state of the light source 970 is maintained.

In other words, the booth 80 may be provided with multiple sensors, such as the open/close sensor S1 and the human sensor 25 described above, the proximity sensor and the human sensor 25 described above, or the seat sensor and the human sensor 25 described above.

In other words, the booth 80 may be provided with multiple detectors that detect the presence or absence of the user inside the frame 81, such that the multiple detectors detect presence or absence according to different detection methods.

Furthermore, in the case where the absence of a user inside the frame 81 is detected by the multiple detectors, the light source 970 may be turned on to start irradiation with ultraviolet light from the light source 970.

Here, the human sensor 25 is given as an example of a first detector among the multiple detectors. The human sensor 25 is a sensor that detects human motion inside the booth 80 to detect the presence or absence of the user inside the booth 80.

Also, the open/close sensor S1 (see FIG. 2) that detects the opening and closing of the door 22 is given as an example of another detector among the multiple detectors.

The open/close sensor S1 detects that the door 22 of the booth 80 has been opened, and thereby detects that the user is not present inside the frame 81.

Specifically, because the door 22 is opened when the user exits the booth 80, by detecting that the door 22 has been opened, the open/close sensor S1 indirectly detects that the user is not present inside the booth 80.

Furthermore, in this case, if the open/close sensor S1 detects that the door 22 has been opened and the human sensor 25 also does not detect human motion, the light source 970 is turned on to start irradiation with ultraviolet light from the light source 970.

Also, the proximity sensor described above is given as another example of the other detector. The proximity sensor detects the user in proximity to the light source 970.

In the case where the other detector is the proximity sensor, if the human sensor 25 does not detect human motion and the proximity sensor also does not detect the user in proximity to the light source 970, the light source 970 is turned on to start irradiation with ultraviolet light from the light source 970.

Also, the seat sensor described above is given as another example of the other detector. The seat sensor is installed in the chair 91 provided inside the booth 80, and detects that the user is sitting in the chair 91.

In the case where the other detector is the seat sensor, if the human sensor 25 does not detect human motion and the seat sensor also detects that the user is sitting, the light source 970 is turned on to start irradiation with ultraviolet light from the light source 970.

(9) Besides the above, multiple light sources 970 that emit ultraviolet light at mutually different wavelengths may be installed in the booth 80, and the light sources 970 may be switched to change the wavelength of the ultraviolet light used to irradiate the interior of the booth 80.

More specifically, for example, a light source 970 that emits ultraviolet light at a wavelength of 254 nm and a light source 970 that emits ultraviolet light at a wavelength of 222 nm are provided.

Furthermore, the light sources 970 may be switched to switch from a state of irradiating with ultraviolet light at a wavelength of either 254 nm or 222 nm to a state of irradiating with ultraviolet light at the other wavelength.

More specifically, for example, when irradiating with ultraviolet light under conditions in which a person is present inside the booth 80, 222 nm ultraviolet light having little effect on the human body is emitted.

Additionally, if the conditions change and a person is no longer present inside the booth 80, the emitted ultraviolet light is switched to 254 nm ultraviolet light, which is more effective for sterilization.

Besides the above, the ultraviolet light to be emitted may also be switched depending on whether the current time is inside or outside the operating hours of the booth 80.

Specifically, for example, if the current time is outside the operating hours of the booth 80 such as in the middle of the night (a time period during which the booth 80 is non-reservable and unavailable for use by the user), the booth 80 is irradiated with ultraviolet light at a wavelength of 254 nm.

On the other hand, if the current time is inside the operating hours of the booth 80 (a time period during which the booth 80 is reservable and available for use by the user), the booth 80 is irradiated with ultraviolet light at a wavelength of 222 nm.

(10) Besides the above, a threshold regarding the ultraviolet light radiation time or radiation energy may be set, and if the ultraviolet light radiation time with respect to the user or the ultraviolet light radiation energy irradiating the user exceeds the predetermined threshold, a process to turn off the light source 970 may be performed.

For example, in the case of using 222 nm ultraviolet light, irradiation with ultraviolet light may be performed even if a person is present inside the booth 80 because the effect on the human body is small, but nevertheless it is preferable to set a threshold as described above.

Additionally, in this case, if the ultraviolet light radiation time with respect to the user or the ultraviolet light radiation energy irradiating the user exceeds the predetermined threshold, the light source 970 is turned off.

Note that the ultraviolet light radiation time with respect to the user may be ascertained by measuring the length of time during which the human sensor 25 detects the user and the light source 970 is also turned on, for example.

Also, the ultraviolet light radiation energy irradiating the user may be obtained by multiplying the length of time during which the human sensor 25 detects the user and the light source 970 is also turned on by the output of the light source 970, for example.

Note that the radiation time and the radiation energy are reset if the user inside the booth 80 changes to another user, such that the radiation time and the radiation energy are ascertained for each user.

Whether or not the user inside the booth 80 has changed to another user may be ascertained by detecting the opening and closing of the door 22 or by ascertaining the faces of individual users through known face recognition technology, for example.

(11) Besides the above, the output of the light source 970 may also be configured to be variable, and furthermore the output of the light source 970 may be varied according to the size of the booth 80.

More specifically, in the case of performing this process, information about the size of the booth 80 is registered in a memory (not illustrated) provided in the booth 80 at the time of factory shipment, for example. Thereafter, a control device provided in the booth 80 sets the output of the light source 970 on the basis of the information registered in the memory.

As another example, an image acquired by the imaging device 24 (see FIG. 2) may be analyzed to ascertain the size of the booth 80, and the output of the light source 970 may be set on the basis of the ascertained size.

Note that each configuration described in the foregoing is not limited to the foregoing exemplary embodiments and exemplary modifications thereof, and is modifiable without departing from the gist of the present disclosure. In other words, it should be understood that various modifications of form and detail are possible without departing from the gist and scope of the claims.

For example, some of the components described in the foregoing may be omitted, and other functions may be added to the components described in the foregoing.

Also, the foregoing describes multiple exemplary embodiments, but the configuration included in one exemplary embodiment may be substituted with the configuration included in another exemplary embodiment, or the configuration included in one exemplary embodiment may be added to another exemplary embodiment.

In the embodiments above, the term "processor" refers to hardware in a broad sense. Examples of the processor include general processors (e.g., CPU: Central Processing Unit) and dedicated processors (e.g., GPU: Graphics Processing Unit, ASIC: Application Specific Integrated Circuit, FPGA: Field Programmable Gate Array, and programmable logic device).

In the embodiments above, the term "processor" is broad enough to encompass one processor or plural processors in collaboration which are located physically apart from each other but may work cooperatively. The order of operations of the processor is not limited to one described in the embodiments above, and may be changed.

The foregoing description of the exemplary embodiments of the present disclosure has been provided for the purposes of illustration and description. It is not intended to be exhaustive or to limit the disclosure to the precise forms disclosed. Obviously, many modifications and variations will be apparent to practitioners skilled in the art. The embodiments were chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. An information processing system comprising:
a processor configured to:
acquire reservation information, the reservation information being information about a reservation of a booth;
determine to improve an air environment by an improvement mechanism in an unused time period on a basis of an elapsed time from a reservation end time of a previous reservation that is a preceding reservation of the booth to a reservation start time of a next reservation that is a succeeding reservation of the booth, the unused time period being a time period between the reservation end time and reservation start time,
in a case where the elapsed time exceeds a predetermined time, determine to increase types of processes to be performed by the improvement mechanism compared to a case where the elapsed time does not exceed the predetermined time, wherein the increased types of processes are performed by the improvement mechanism based on the determination that the elapsed time exceeds the predetermined time.

2. The information processing system according to claim 1, wherein the processor is further configured to:

determine to improve the air environment with the improvement mechanism in a time period in which the booth is not reserved.

3. The information processing system according to claim 1, wherein the processor is configured to: determine that a specific process is to be performed by the improvement mechanism in the case where the elapsed time exceeds the predetermined time.

4. The information processing system according to claim 1, wherein the processor is configured to:

make a determination regarding a frequency of the improvement of the air environment by the improvement mechanism on a basis of the acquired reservation information.

5. The information processing system according to claim 1, wherein the processor is configured to:

make a determination regarding a degree of the improvement of the air environment by the improvement mechanism on a basis of the acquired reservation information.

6. A non-transitory computer readable medium storing a program causing a computer to execute a process for improving an air environment inside a booth, the process comprising:

acquiring reservation information, the reservation information being information about a reservation of the booth;

determining to improve an air environment by an improvement mechanism in an unused time period on a basis of an elapsed time from a reservation end time of a previous reservation that is a preceding reservation of the booth to a reservation start time of a next reservation that is a succeeding reservation of the booth, the unused time period being a time period between the reservation end time and reservation start time, in a case where the elapsed time exceeds a predetermined time, determine to increase types of processes to be performed by the improvement mechanism compared to a case where the elapsed time does not exceed the predetermined time, wherein the increased types of processes are performed by the improvement mechanism based on the determination that the elapsed time exceeds the predetermined time.

* * * * *